United States Patent
Sun

(10) Patent No.: US 11,413,265 B2
(45) Date of Patent: Aug. 16, 2022

(54) FORMULATIONS AND COMPOSITIONS OF CABAZITAXEL

(71) Applicant: Zhuhai Beihai Biotech Co., Ltd., Guangdong (CN)

(72) Inventor: Qun Sun, Princeton, NJ (US)

(73) Assignee: Zhuhai Beihai Biotech Co., Ltd., Zhuhai (CN)

( * ) Notice: Subject to any disclaimer, the term of this patent is extended or adjusted under 35 U.S.C. 154(b) by 72 days.

(21) Appl. No.: 16/982,252

(22) PCT Filed: Apr. 19, 2019

(86) PCT No.: PCT/US2019/028337
§ 371 (c)(1),
(2) Date: Sep. 18, 2020

(87) PCT Pub. No.: WO2019/204738
PCT Pub. Date: Oct. 24, 2019

(65) Prior Publication Data
US 2021/0052540 A1    Feb. 25, 2021

Related U.S. Application Data

(60) Provisional application No. 62/834,767, filed on Apr. 16, 2019, provisional application No. 62/660,584, filed on Apr. 20, 2018.

(51) Int. Cl.
| | | |
|---|---|---|
| *A61K 31/335* | (2006.01) | |
| *A61P 35/00* | (2006.01) | |
| *A61K 31/337* | (2006.01) | |
| *A61K 31/198* | (2006.01) | |
| *A61K 38/38* | (2006.01) | |
| *A61K 9/08* | (2006.01) | |

(52) U.S. Cl.
CPC .......... *A61K 31/337* (2013.01); *A61K 31/198* (2013.01); *A61K 38/385* (2013.01); *A61K 9/08* (2013.01)

(58) Field of Classification Search
CPC ........ A61K 31/335; A61K 31/19; A61P 35/00
USPC ................................................ 514/449, 565
See application file for complete search history.

(56) References Cited

U.S. PATENT DOCUMENTS

| | | |
|---|---|---|
| 6,506,405 B1 | 1/2003 | Soon-Shiong et al. |
| 8,735,611 B2 | 5/2014 | Henschke et al. |
| 8,901,322 B2 | 12/2014 | Lahiri et al. |
| 9,012,665 B2 | 4/2015 | Kung et al. |
| 9,199,953 B2 | 12/2015 | Lahiri et al. |
| 9,309,210 B2 | 4/2016 | Didier et al. |
| 9,353,076 B2 | 5/2016 | Li et al. |
| 9,394,266 B2 | 7/2016 | Vraspir et al. |
| 2005/0282734 A1 | 12/2005 | Kadima et al. |
| 2012/0076862 A1 | 3/2012 | Desai et al. |
| 2015/0141673 A1 | 5/2015 | Song et al. |
| 2015/0315164 A1 | 11/2015 | Rampalli et al. |
| 2016/0000726 A1 | 1/2016 | Li et al. |
| 2016/0244420 A1 | 8/2016 | Cabri et al. |
| 2016/0257663 A1 | 9/2016 | Cabri et al. |
| 2016/0340327 A1 | 11/2016 | Rampalli et al. |
| 2019/0083448 A1 | 3/2019 | Sun |
| 2020/0345681 A1 | 11/2020 | Sun |

FOREIGN PATENT DOCUMENTS

| | | |
|---|---|---|
| CN | 103393632 | 11/2013 |
| CN | 104224750 | 12/2014 |
| CN | 104490797 | 4/2015 |
| CN | 105012251 | 11/2015 |
| CN | 105727303 | 7/2016 |
| CN | 106852911 | 6/2017 |
| WO | WO 2014067207 | 5/2014 |
| WO | WO 2014115168 | 7/2014 |
| WO | WO 2014128728 | 8/2014 |
| WO | WO 2015058960 | 4/2015 |
| WO | WO 2015087228 | 6/2015 |
| WO | WO 2018059304 | 4/2018 |
| WO | WO 2017123760 | 1/2020 |

OTHER PUBLICATIONS

Bosse et al.,"Phase I Comparability of Recombinant Human Albumin and Human Serum Albumin," J Clin. Pharmacol., Jan. 2005, 45(1):57-67.
Briggs et al., "An adverse reaction to the administration of disoprofol", Anesthesia, Nov. 1982, 37(11): 1099-1101.
Bruno R et al., "Population pharmacokinetics/pharmacodynamics of docetaxel in phase II studies in patients with cancer," J Clin Oncol Jan. 1998, 16(1): 187-96.
Carter et al., "Structure of serum albumin.", Adv. Protein. Chem. ,1994, 45:153-203.
Chen Z et al., "Human serum albumin from recombinant DNA technology: Challenges and strategies," Biochimica et Biophysica Acta Dec. 2013, 1830(12):5515-5525.
Chen, "Removal of fatty acids from semm albumin by charcoal treatment.", J. Biol. Chem. Jan. 1967, 242: 173-181.
Cohn et al., "Preparation and properties of serum and plasma proteins; a system for the separation into fractions of the protein and lipoprotein components of biological tissues and fluids.", J. Am. Chem. Soc., Mar. 1946, 68: 459-475.
Curry et al., "Crystal structure of human serum albumin complexed with fatty acid reveals an asymmetric distribution of binding sites.", Nat. Struct. Biol., Sep. 1998, 5(9) 827-35.

(Continued)

*Primary Examiner* — Raymond J Henley, III
(74) *Attorney, Agent, or Firm* — Fish & Richardson P.C.

(57) ABSTRACT

This document relates to a composition comprising Cabazitaxel, or a pharmaceutically acceptable salt thereof, human serum albumin, and arginine, or a pharmaceutically acceptable salt thereof, wherein the human serum albumin and the Cabazitaxel, or a pharmaceutically acceptable salt thereof, in the composition have a ratio by weight of no less than 120:1. This document also relates to methods to prepare a composition comprising Cabazitaxel, or a pharmaceutically acceptable salt thereof, human serum albumin, and arginine, or a pharmaceutically acceptable salt thereof, as described herein.

19 Claims, No Drawings

(56) References Cited

OTHER PUBLICATIONS

Curry et al., "Fatty acid binding to human serum albumin: new insights from crystallographic studies", Biochemica et Biophysica Acta., Nov. 1999,1441, 131-140.
Extended European Search Report in U.S. Appl. No. 17/738,932, dated Jan. 18, 2019.
Fehske et al., "The location of drug binding sites in human serum albumin.", Biochem. Pharmcol., Apr. 1981, 30, 687-92.
Finlayson, J.S.: Albumin Products. "Seminars in Thrombosis and Hemostasis," Thieme Medical Publishers Inc., 1980, 6(2):85-120.
Hauser et al., "Oxygen transport responses to colloids and crystalloids in critically ill surgical patients.", Surgery, Gynecology and Obstetrics, 1980, 150, 811-816.
He et al., "Atomic structure and chemistiy of human serum albumin," Nature, Jul. 1992, 358, 209-15.
International Search Report and Written Opinion for App. Ser. No. PCT/US17/13194, dated Mar. 30, 2017, 11 pages.
International Search Report and Written Opinion in International Appl No. PCT/US2019/028337, dated Jun. 25, 2019, 9 pages.
Kragh-Hansen, "Structure- and ligand binding properties of human serum albumin", Dan. Med Bull.,1990, 1441, 131-40.
Lee et al. "An intravenous formulation decision tree for discovery compound formulation development.", International Journal of Pharmaceutics, Mar. 2003, (6)253,111-119.
Lin et al., Stability of human serum albumin during bioprocessing: denaturation and aggregation during processing of albumin paste. Mar. 2000, Pharmaceutical Research 17: 391-6.
Piccart MJ et al., "Docetaxel: an Active New Drug for Treatment of Advanced Epithelial Ovarian Cancer," JNCI Journal of the Natl Cancer Inst,May 1995, 87(9):676-681.
Sugio et al., "Crystal structure of human serum albumin at 2.5 A resolution.", Jun. 1999, Protein. Eng., 12, 439-46.
Trudeau et al., "Docetaxel in patients with metastatic breast cancer: a phase II study of the National Cancer Institute of Canada-Clinical Trials Group.", J. Clin, Oncol., Feb. 1996, 14(2): 422-8.
Tullis, "Albumin. 1. Background and use.", Jan. 1977, JAMA, 237, 355-360, 460-463.
Vorum, "Reversible ligand binding to human serum albumin. Theoretical and clinical aspects.", Dan. Med. Bull., Nov. 1999, 46, 379-99.
Waugh et al., "Stability, compatibility, and plasticizer extraction of taxol (NSC-125973) injection diluted in infusion solutions and stored in various containers.", Am. J. Hosp. Pharmacists, Jul. 1991, 48(7): 1520-4.
PCT International Preliminary Report on Patentability in International Appln. No. PCT/US2019/028337, dated Oct. 20, 2020, 7 pages.

FORMULATIONS AND COMPOSITIONS OF CABAZITAXEL

CLAIM OF PRIORITY

This application is a National Stage Application under 35 U.S.C. § 371 and claims the benefit of International Application No. PCT/US2019/028337, filed Apr. 19, 2019, which claims priority to U.S. provisional patent application No. 62/660,584, filed on Apr. 20, 2018 and U.S. provisional patent application Ser. No. 62/834,767, filed on Apr. 16, 2019, the entire contents of which are hereby incorporated by reference in their entirety.

TECHNICAL FIELD

This document relates to formulations and compositions for the treatment of proliferative diseases, more particularly to formulations and compositions comprising Cabazitaxel and human serum albumin that are useful in treating cancer.

BACKGROUND

Many drugs for parenteral use are insoluble in water, and are thus formulated with solubilizing agents, surfactants, solvents, and/or emulsifiers that are irritating, allergenic, or toxic when administered to patients. See, e.g., Briggs et al., *Anesthesis* 37, 1099 (1982), and Waugh et al., *Am. J. Hosp. Pharmacists*, 48, 1520 (1991)). Further, many of these drugs, especially those administered intravenously, cause undesirable side effects such as venous irritation, phlebitis, burning and pain on injection, venous thrombosis, extravasation, and other administration related side effects. Additionally, often free drugs present in formulations induce pain or irritation upon administration.

Taxanes play an important role in the treatment of various solid tumors. Cabazitaxel (trade name Jevtana®) is a semi-synthetic taxane derivative. It was developed by Sanofi-Aventis and was approved by the U.S. FDA for the treatment of hormone-refractory prostate cancer on Jun. 17, 2010. Cabazitaxel in combination with prednisone is a treatment option for hormone-refractory prostate cancer following cabazitaxel-based treatment. JEVTANA is supplied as a kit consisting of (a) a JEVTANA injection, which contains 60 mg cabazitaxel in 1.5 mL polysorbate 80; and (b) a diluent, containing approximately 5.7 mL 13% (W/W) ethanol. Prior to administration, the JEVTANA injection must first be mixed with the diluent, which dilutes the amount of Cabazitaxel to 10 mg/mL, and then further diluted with either 0.9% sodium chloride solution or 5% dextrose solution for infusion. See JEVTANA Prescribing Information.

Other taxane compounds include cabazitaxel, which is marketed as Taxotere® and is FDA-approved for breast cancer, non-small cell lung cancer, hormone refractory prostate cancer, gastric adenocarcinoma, and squamous cell carcinoma of head and neck cancer. The clinical intravenous administration of commercially available cabazitaxel (Taxotere®) is formulated in a highly concentrated solution containing 40 mg cabazitaxel and 1040 mg Polysorbate 80 per mL. See TAXOTERE Prescribing Information.

The presence of polysorbate 80 in JEVTANA, as well as TAXOTERE, can result in serious side effects. It has been reported that cabazitaxel administration is associated with the occurrence of unpredictable (acute) hypersensitivity reactions and cumulative fluid retention. See, e.g., Trudeau M E et al., *J Clin Oncol* 1996; 14:422-8, Piccart M J et al., *J Natl Cancer Inst* 1995; 87:676-81, Bruno R et al., *J Clin Oncol* 1998; 16:187-96. These side-effects have been attributed, in part, to the presence of polysorbate 80.

In order to reduce the side effects induced by polysorbate 80, patients may be treated with dexamethasone prior to each dose of JEVTANA. Dexamethasone is a steroid that suppresses the immune response in patients, which can be especially detrimental in cancer patients under chemotherapy, whose immunity may already be compromised due to the destruction of healthy cells by the chemotherapeutic treatment. As a result, these patients can be susceptible to bacterial and fungal infections. Further, despite receiving the dexamethasone pre-medication, patients can report hypersensitivity side effects from the taxane compound treatment. Due to these side effects, patients may stop taxane compound therapy, skip a dose, or continue further therapy at a reduced dose.

New formulations of cabazitaxel without polysorbate 80 have been reported. WO2017/123760 describes compositions and formulations including cabazitaxel and human serum albumin. China patent applications CN104490797A, CN104224750A, CN103393632A, CN106852911A, and CN105727303A describes nanoparticle compositions of cabazitaxel and albumin.

Novel formulations of cabazitaxel are further needed to avoid these side effects, pre-medication requirements, and patient noncompliance issues associated with the currently marketed formulation.

SUMMARY

Provided herein is a composition comprising Cabazitaxel, human serum albumin, and arginine, wherein the human serum albumin and the Cabazitaxel in the composition have a ratio by weight of no less than 120:1. In some embodiments, arginine and the Cabazitaxel in the composition have a ratio by weight of no less than 1:1.

In some embodiments, the human serum albumin and the Cabazitaxel in the composition have a ratio by weight of no less than about 150:1. In some embodiments, the human serum albumin and the Cabazitaxel in the composition have a ratio by weight of no less than about 200:1. In some embodiments, the human serum albumin and the Cabazitaxel in the composition have a ratio by weight of no less than about 300:1. In some embodiments, the Cabazitaxel and the human serum albumin in the composition are in a ratio by weight from about 1:250 to about 1:600. In some embodiments, the Cabazitaxel and the human serum albumin in the composition are in a ratio by weight from about 1:300 to about 1:800. In some embodiments, the Cabazitaxel and the human serum albumin in the composition are in a ratio by weight from about 1:300 to about 1:500. In some embodiments, the Cabazitaxel and the human serum albumin in the composition are in a ratio by weight from about 1:320 to about 1:450. In some embodiments, the Cabazitaxel and the human serum albumin in the composition are in a ratio by weight from about 1:320 to about 1:400. In some embodiments, the Cabazitaxel and the human serum albumin in the composition are in a ratio by weight from about 1:320 to about 1:380. In some embodiments, the Cabazitaxel and the human serum albumin in the composition are in a ratio by weight from about 1:330 to about 1:500. In some embodiments, the Cabazitaxel and the human serum albumin in the composition are in a ratio by weight from about 1:330 to about 1:450. In some embodiments, the Cabazitaxel and the human serum albumin in the composition are in a ratio by weight from about 1:330 to about 1:400. In some embodiments, the Cabazitaxel and the human serum albumin in the composition are in a ratio by weight from about 1:330 to about 1:350. In some embodiments, the Cabazitaxel and the human serum albumin in the composition are in a ratio by weight from about 1:340 to about 1:500. In some embodiments, the Cabazitaxel and the human serum albumin in the composition are in a ratio by weight from about 1:340 to about 1:450. In some embodiments, the Cabazitaxel and the human serum albumin in the composition are in a ratio by weight from about 1:340 to about 1:400. In some embodiments, the Cabazitaxel and the human serum albumin in the composition are in a ratio by weight from about 1:340 to about 1:360. In some embodiments, the Cabazitaxel and the human serum albumin in the composition are in a ratio by weight from about 1:340 to about 1:350. In some embodiments, the Cabazitaxel and the human serum albumin in the composition are in a ratio by weight from about 1:335 to about 1:360. In some embodiments, the Cabazitaxel and the human serum albumin in the composition are in a ratio by weight of about 1:300, about 1:310, about 1:320, about 1:330, about 1:340, about 1:350, about 1:360, about 1:370, about 1:380, about 1:390, or about 1:400. In some embodiments, the Cabazitaxel and the human serum albumin in the composition are in a ratio by weight of about 1:700, about 1:740, about 1:750, or about 1:800. In some embodiments, the Cabazitaxel and the human serum albumin in the composition are in a ratio by weight of about 1:330. In some embodiments, the Cabazitaxel and the human serum albumin in the composition are in a ratio by weight of about 1:340. In some embodiments, the Cabazitaxel and the human serum albumin in the composition are in a ratio by weight of about 1:350. In some embodiments, the Cabazitaxel and the human serum albumin in the composition are in a ratio by weight of about 1:360.

In some embodiments, arginine and Cabazitaxel in the composition have a ratio by weight of no less than about 2:1. In some embodiments, arginine and Cabazitaxel in the composition have a ratio by weight of no less than about 3:1. In some embodiments, arginine and Cabazitaxel in the composition have a ratio by weight of no less than about 5:1. In some embodiments, arginine and Cabazitaxel in the composition have a ratio by weight of no less than about 10:1. In some embodiments, arginine and Cabazitaxel in the composition have a ratio by weight of no less than about 15:1. In some embodiments, arginine and Cabazitaxel in the composition have a ratio by weight of about 8:1. In some embodiments, arginine and Cabazitaxel in the composition have a ratio by weight of 10:1. In some embodiments, arginine and Cabazitaxel in the composition have a ratio by weight of 15:1.

In some embodiments, the human serum albumin is a native human serum albumin. In some embodiments, the human serum albumin is a native human serum albumin obtained from pools of human plasma. In some embodiments, the human serum albumin is a recombinant human serum albumin. In some embodiments, the human serum albumin is a fatty acid free human serum albumin. In some embodiments, the human serum albumin is essentially fatty acid free.

In some embodiments, the composition is a solid formulation. In some embodiments, the composition is an aqueous formulation. In some embodiments, the aqueous formulation is substantially free of solvent other than water. In some embodiments, the aqueous formulation is a clear aqueous solution.

Also, provided herein is a pharmaceutical composition comprising Cabazitaxel, human serum albumin, and arginine as described herein, and a pharmaceutically acceptable carrier.

Also, provided herein is a method of treating cancer comprising the step of administering to a subject in need thereof a therapeutically effective amount of a pharmaceutical composition comprising the composition comprising Cabazitaxel, human serum albumin, and arginine as described herein, and a pharmaceutically acceptable carrier.

In some embodiments, the cancer is a solid tumor cancer. In some embodiments, the cancer is a prostate cancer.

In some embodiments, the method of treating a prostate cancer comprises the step of administering to a subject in need thereof of a therapeutically effective amount of a pharmaceutical composition comprising the composition comprising the cabazitaxel and the human serum albumin as described herein, prednisone, and a pharmaceutically acceptable carrier.

DETAILED DESCRIPTION

Provided herein is a composition comprising Cabazitaxel, human serum albumin, and arginine, wherein the human serum albumin and the Cabazitaxel in the composition have a ratio by weight of no less than 120:1. In some embodiments, arginine and the Cabazitaxel in the composition have a ratio by weight of no less than 1:1.

In some embodiments, the human serum albumin and the Cabazitaxel in the composition have a ratio by weight of no less than about 150:1. In some embodiments, the human serum albumin and the Cabazitaxel in the composition have a ratio by weight of no less than about 200:1. In some embodiments, the human serum albumin and the Cabazitaxel in the composition have a ratio by weight of no less than about 250:1. In some embodiments, the human serum albumin and the Cabazitaxel in the composition have a ratio by weight of no less than about 300:1. In some embodiments, the Cabazitaxel and the human serum albumin in the composition are in a ratio by weight from about 1:250 to about 1:600. In some embodiments, the Cabazitaxel and the human serum albumin in the composition are in a ratio by weight from about 1:300 to about 1:500. In some embodiments, the Cabazitaxel and the human serum albumin in the composition are in a ratio by weight from about 1:300 to about 1:400. In some embodiments, the Cabazitaxel and the human serum albumin in the composition are in a ratio by weight from about 1:320 to about 1:450. In some embodiments, the Cabazitaxel and the human serum albumin in the composition are in a ratio by weight from about 1:320 to about 1:400. In some embodiments, the Cabazitaxel and the human serum albumin in the composition are in a ratio by weight from about 1:320 to about 1:380. In some embodiments, the Cabazitaxel and the human serum albumin in the composition are in a ratio by weight from about 1:330 to about 1:500. In some embodiments, the Cabazitaxel and the human serum albumin in the composition are in a ratio by weight from about 2:330 to about 1:450. In some embodiments, the Cabazitaxel and the human serum albumin in the composition are in a ratio by weight from about 1:330 to about 1:400. In some embodiments, the Cabazitaxel and the human serum albumin in the composition are in a ratio by weight from about 1:330 to about 1:350. In some embodiments, the Cabazitaxel and the human serum albumin in the composition are in a ratio by weight from about 1:340 to about 1:500. In some embodiments, the Cabazitaxel and the human serum albumin in the composition are in a ratio by weight from about 1:300 to about 1:800. In some embodiments, the Cabazitaxel and the human serum albumin in the composition are in a ratio by weight from about 1:340 to about 1:450. In some embodiments, the Cabazitaxel and the human serum albumin in the composition are in a ratio by weight from about 1:340 to about 1:400. In some embodiments, the Cabazitaxel and the human serum albumin in the composition are in a ratio by weight from about 1:340 to about 1:360. In some embodiments, the Cabazitaxel and the human serum albumin in the composition are in a ratio by weight from about 1:340 to about 1:350. In some embodiments, the Cabazitaxel and the human serum albumin in the composition are in a ratio by weight from about 1:335 to about 1:360. In some embodiments, the Cabazitaxel and the human serum albumin in the composition are in a ratio by weight of about 1:300, about 1:310, about 1:320, about 1:330, about 1:340, about 1:350, about 1:360, about 1:370, about 1:380, about 1:390, or about 1:400. In some embodiments, the Cabazitaxel and the human serum albumin in the composition are in a ratio by weight of about 1:500, about 1:600, about 1:650, about 1:700, about 1:740, about 1:750, or about 1:800. In some embodiments, the Cabazitaxel and the human serum albumin in the composition are in a ratio by weight of about 1:330. In some embodiments, the Cabazitaxel and the human serum albumin in the composition are in a ratio by weight of about 1:340. In some embodiments, the Cabazitaxel and the human serum albumin in the composition are in a ratio by weight of about 1:350. In some embodiments, the Cabazitaxel and the human serum albumin in the composition are in a ratio by weight of about 1:360.

In some embodiments, arginine and Cabazitaxel in the composition have a ratio by weight of no less than about 2:1. In some embodiments, arginine and Cabazitaxel in the composition have a ratio by weight of no less than about 3:1. In some embodiments, arginine and Cabazitaxel in the composition have a ratio by weight of no less than about 5:1. In some embodiments, arginine and Cabazitaxel in the composition have a ratio by weight of no less than about 10:1. In some embodiments, arginine and Cabazitaxel in the composition have a ratio by weight of no less than about 15:1. In some embodiments, arginine and Cabazitaxel in the composition have a ratio by weight of about 6:1, about 7:1, about 8:1, about 9:1, about 10:1, about 11:1, about 12:1, about 13:1, about 14:1, about 15:1, about 16:1, about 17:1, about 18:1, about 19:1, about 20:1, about 25:1, about 30:1, or about 40:1.

In some embodiments, arginine and Cabazitaxel in the composition have a ratio by weight from about 0.5:1 to about 200:1. In some embodiments, arginine and Cabazitaxel in the composition have a ratio by weight from about 1:1 to about 100:1. In some embodiments, arginine and Cabazitaxel in the composition have a ratio by weight from about 1:1 to about 200:1. In some embodiments, arginine and Cabazitaxel in the composition have a ratio by weight from about 10:1 to about 200:1. In some embodiments, arginine and Cabazitaxel in the composition have a ratio by weight from about 15:1 to about 200:1. In some embodiments, arginine and Cabazitaxel in the composition have a ratio by weight from about 1:1 to about 150:1. In some embodiments, arginine and Cabazitaxel in the composition have a ratio by weight from about 1:1 to about 100:1. In some embodiments, arginine and Cabazitaxel in the composition have a ratio by weight from about 5:1 to about 150:1. In some embodiments, arginine and Cabazitaxel in the composition have a ratio by weight from about 5:1 to about 100:1. In some embodiments, arginine and Cabazitaxel in the composition have a ratio by weight from about 10:1 to about 150:1. In some embodiments, arginine and Cabazitaxel in the composition have a ratio by weight from about 10:1 to about 100:1. In some embodiments, arginine and Cabazitaxel in the composition have a ratio by weight from about 15:1 to about 150:1. In some embodiments, arginine and Cabazitaxel in the composition have a ratio by weight from about 15:1 to about 100:1. In some embodiments, arginine and Cabazitaxel in the composition have a ratio by weight from about 2:1 to about 50:1. In some embodiments, arginine and Cabazitaxel in the composition have a ratio by weight from about 3:1 to about 30:1. In some embodiments, arginine and Cabazitaxel in the composition have a ratio by weight from about 5:1 to about 25:1. In some embodiments, arginine and Cabazitaxel in the composition have a ratio by weight from about 6:1 to about 20:1. In some embodiments, arginine and Cabazitaxel in the composition have a ratio by weight from about 1:1 to about 20:1. In some embodiments, arginine and Cabazitaxel in the composition have a ratio by weight from about 1:1 to about 30:1.

As used herein, the term "human serum albumin" refers to native and recombinant human serum albumin. Native human serum albumin and other plasma proteins can be precipitated from human plasma by varying the pH and adding ethanol, in what is known as the Cohn fractionation process (see, e.g., Cohn E J et al., *J. Am. Chem. Soc.* 1946; 68:459-475). By controlling the pH and ethanol content, semi-purified fractions of plasma proteins can be produced. One of the last proteins to precipitate in the Cohn process is native human serum albumin. After precipitation, a wet paste of crude native human serum albumin is obtained. Subsequent bioprocessing steps (purification, filtration, pasteurization, etc.) can be used to produce a purified, stabilized form of native human serum albumin for commercial use (see, e.g., Lin J J et al., *Pharmaceutical Research* 2000; 17:391-6). Recombinant human serum albumin is a highly purified animal-, virus-, and prion-free product as alternative to native human serum albumin, to which it is structurally equivalent (see, e.g., Bosse D et al., *J Clin. Pharmacol.* 2005; 45:57-67). Recombinant human serum albumin has been produced by various hosts, both prokaryotic and eukaryotic (see, e.g., Chen Z et al., *Biochimica et Biophysica Acta* 2013; 1830:5515-5525).

Human serum albumin (HSA) is a highly soluble globular protein of $M_r$ 65K and consists of 585 amino acids. HSA is the most abundant protein in the plasma and accounts for 70-80% of the colloid osmotic pressure of human plasma. The amino acid sequence of HSA contains a total of 17 disulphide bridges, one free thiol (Cys 34), and a single tryptophan (Trp 214). Intravenous use of HSA solution has been indicated for the prevention and treatment of hypovolumic shock (see, e.g., Tullis, *JAMA,* 237, 355-360, 460-463, (1977) and Houser et al., Surgery, *Gynecology and Obstetrics,* 150, 811-816 (1980)) and in conjunction with exchange transfusion in the treatment of neonatal hyperbilirubinemia (see, e.g., Finlayson, *Seminars in Thrombosis and Hemostasis,* 6, 85-120, (1980)).

Human serum albumin (HSA) has multiple hydrophobic binding sites (a total of seven for medium and long-chain fatty acids, an endogenous ligand of HSA) and binds a diverse set of drugs, especially neutral and negatively charged hydrophobic compounds (see, e.g., Goodman et al., *The Pharmacological Basis of Therapeutics,* 9th ed, McGraw-Hill New York (1996)). Two high affinity binding sites have been proposed in subdomains IIA and IIIA of HSA, which are highly elongated hydrophobic pockets with charged lysine and arginine residues near the surface which function as attachment points for polar ligand features (see, e.g., Fehske et al., *Biochem. Pharmcol.*, 30, 687-92 (1981), Vorum, *Dan. Med. Bull.*, 46, 379-99 (1999), Kragh-Hansen, Dan. *Med Bull.*, 1441, 131-40 (1990), Curry et al., *Nat. Struct. Biol.*, 5, 827-35 (1998), Sugio et al., *Protein. Eng.*, 12, 439-46 (1999), He et al., *Nature*, 358, 209-15 (1992), and Carter et al., *Adv. Protein. Chem.*, 45, 153-203 (1994)).

In some embodiments, the human serum albumin is a native human serum albumin. In some embodiments, the human serum albumin is a native human serum albumin obtained from pools of human plasma. In some embodiments, the human serum albumin is a recombinant human serum albumin. In some embodiments, the human serum albumin is a fatty acid free human serum albumin. In some embodiments, the human serum albumin is essentially fatty acid free.

Solutions of human serum albumin for infusion are commercially available. Those solutions must be supplemented with stabilizers to allow pasteurization and storage, to avoid the spontaneous polymerization of the albumin. Usually, N-acetyltryptophan and caprylic acid or their sodium salts are used in alone or in combination as the stabilizers.

In some embodiments, the human serum albumin is a commercially available solution of human serum albumin USP for infusion. In some embodiments, the human serum albumin comprises a commercially available solution of human serum albumin USP for infusion. In some embodiments, the human serum albumin is a lyophilized form of a commercially available solution of human serum albumin USP for infusion. In some embodiments, the human serum albumin is a lyophilized powder obtained by lyophilizing a commercially available solution of human serum albumin USP for infusion. In some embodiments, a commercially available solution of human serum albumin USP for infusion is used as the source of the human serum albumin. In some embodiments, the solution of human serum albumin USP for infusion is 5% solution of human serum albumin USP (w/v). In some embodiments, the solution of human serum albumin USP for infusion is 20% solution of human serum albumin USP (w/v). In some embodiments, the solution of human serum albumin USP for infusion is 25% solution of human serum albumin USP (w/v). In some embodiments, the human serum albumin is an aqueous solution prepared by diluting a commercially available solution of human serum albumin USP for infusion. In some embodiments, the human serum albumin is an aqueous solution prepared by diluting a commercially available solution of human serum albumin USP for infusion with water. In some embodiments, the human serum albumin is a lyophilized powder prepared from a commercially available solution of human serum albumin USP for infusion.

In some embodiments, the composition comprises at least one stabilizer for the human serum albumin. In some embodiments, the composition comprises two stabilizers for the human serum albumin. In some embodiments, the stabilizers are N-acetyltryptophan, or a pharmaceutically acceptable salt thereof, and caprylic acid, or a pharmaceutically acceptable salt thereof (e.g., sodium salt thereof). In some embodiments, the stabilizer is N-acetyltryptophan, or a pharmaceutically acceptable salt thereof (e.g., sodium salt thereof). In some embodiments, the stabilizer is caprylic acid, or a pharmaceutically acceptable salt thereof (e.g., sodium salt thereof).

In vitro, the binding of cabazitaxel to human serum proteins was 89 to 92% and was not saturable up to 50,000 ng/mL, which covers the maximum concentration observed in clinical trials. Cabazitaxel is mainly bound to human serum albumin (82%). See JEVTANA Prescribing Information.

As used herein the term "cabazitaxel" is a compound that has the CAS No. 183133-96-2 and the following chemical structure:

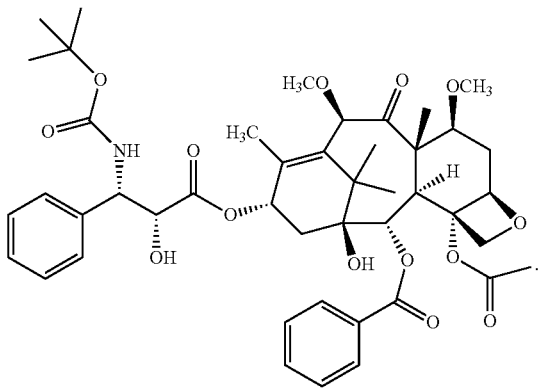

Cabazitaxel is lipophilic, practically insoluble in water and soluble in alcohol.

Further, cabazitaxel is a microtubule inhibitor indicated in combination with prednisone for treatment of patients with hormone-refractory metastatic prostate cancer previously treated with a cabazitaxel-containing treatment regimen.

In some embodiments, the term "cabazitaxel" refers to a pharmaceutically acceptable salt of cabazitaxel.

As used herein, the term "pharmaceutically acceptable salts" refers to salts that retain the desired biological activity of a compound (e.g., cabazitaxel, arginine) and exhibit minimal undesired toxicological effects. These pharmaceutically acceptable salts may be prepared in situ during the final isolation and purification of the compound, or by separately reacting the purified compound in its free acid or free base form with a suitable base or acid, respectively. In some embodiments, pharmaceutically acceptable salts may be preferred over the respective free base or free acid because such salts impart greater stability or solubility to the molecule thereby facilitating formulation into a dosage form. Basic compounds are generally capable of forming pharmaceutically acceptable acid addition salts by treatment with a suitable acid. Suitable acids include pharmaceutically acceptable inorganic acids and pharmaceutically acceptable organic acids. Representative pharmaceutically acceptable acid addition salts include hydrochloride, hydrobromide, nitrate, methylnitrate, sulfate, bisulfate, sulfamate, phosphate, acetate, hydroxyacetate, phenylacetate, propionate, butyrate, isobutyrate, valerate, maleate, hydroxymaleate, acrylate, fumarate, malate, tartrate, citrate, salicylate, p-aminosalicyclate, glycollate, lactate, heptanoate, phthalate, oxalate, succinate, benzoate, o-acetoxybenzoate, chlorobenzoate, methylbenzoate, dinitrobenzoate, hydroxybenzoate, methoxybenzoate, mandelate, tannate, formate, stearate, ascorbate, palmitate, oleate, pyruvate, pamoate, malonate, laurate, glutarate, glutamate, estolate, methanesulfonate (mesylate), ethanesulfonate (esylate), 2-hydroxyethanesulfonate, benzenesulfonate (besylate), p-aminobenzenesulfonate, p-toluenesulfonate (tosylate), napthalene-2-sulfonate, ethanedisulfonate, hydrogen bisulfide, bitartrate, gluconate, glucuronate, para-bromophenylsulfonate, carbonate, pyrosulfate, sulfite, bisulfate, monohydrogen phosphate, dihydrogen phosphate, metaphosphate, pyrophosphate, chloride, bromide, iodide, decanoate, caprylate, caprate, propiolate, suberate, sebacate, butyne-1,4-dioate, hexyne-1,6-dioate, terephthalate, sulfonate, xylenesulfonate, phenylpropionate, phenylbutyrate, β-hydroxybutyrate, glycolate, propanesulfonate, naphthalene-1-sulfonate, naphthalene-2-sulfonate and 2,5-dihydroxybenzoate. Suitable bases include pharmaceutically acceptable inorganic bases and pharmaceutically acceptable organic bases. Representative pharmaceutically acceptable base addition salts include hydroxide of alkali metals including sodium, potassium, and lithium; hydroxides of alkaline earth metals such as calcium and magnesium; hydroxides of other metals, such as aluminum and zinc; ammonia, organic amines such as unsubstituted or hydroxyl-substituted mono-, di-, or tri-alkylamines, dicyclohexylamine; tributyl amine; pyridine; N-methyl, N-ethylamine; diethylamine; triethylamine; mono-, bis-, or tris-(2-OH—($C_1$-$C_6$)-alkylamine), such as N,N-dimethyl-N-(2-hydroxyethyl)amine or tri-(2-hydroxyethyl)amine; N-methyl-D-glucamine; morpholine; thiomorpholine; piperidine; pyrrolidine; and amino acids such as arginine, lysine, and the like.

In some embodiments, the cabazitaxel can be a cabazitaxel with one equivalent of the acetone solvate. In some embodiments, cabazitaxel, or a salt thereof, may be crystalline or amorphous. In some embodiments, cabazitaxel, or a salt thereof, may be in a form of a hydrate. In some embodiments, the cabazitaxel can be any one of cabazitaxel solvates, hydrates, and/or crystal forms disclosed, for example, in US application publication No. 20150315164, US application publication No. 20160257663, US application publication No. 20160340327, US application publication No. 20160244420, US application publication No. 20150141673, U.S. Pat. Nos. 9,012,665, 9,353,076, 9,394,266, 9,309,210, 9,199,953, 8,735,611, 8,735,611, 8,901,322, PCT publication No. WO2014115168, PCT publication No. WO2015087228, PCT publication No. WO2014067207, PCT publication No. WO2014128728 or PCT publication No. WO2015058960, the disclosures of each of the above are incorporated herein by reference in their entirety.

As used herein, the term "arginine" refers to a compound that has the following chemical structure:

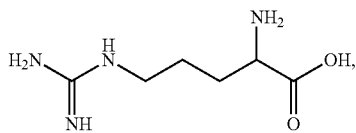 [SMILES: N=C(N)NCCCC(N)C(=O)O]

or a pharmaceutically acceptable salt thereof.

In some embodiments, arginine is L-arginine. The CAS Registry No. for L-arginine is 74-79-3. In some embodiments, arginine is D-arginine. The CAS Registry No. for D-arginine is 157-06-2. In some embodiments, arginine is a mixture of L-arginine and D-arginine. In some embodiments, arginine is DL-arginine. The CAS Registry No. for DL-arginine is 7200-25-1.

In some embodiments, the term "arginine" encompasses a pharmaceutically acceptable salt of arginine. In some embodiments, the term "arginine" encompasses a pharmaceutically acceptable salt of L-arginine. In some embodiments, arginine can be a hydrochloride salt of L-arginine. The preferred arginine is L-arginine, or a pharmaceutically acceptable salt thereof.

Formulations suitable for parenteral administration include aqueous and non-aqueous, isotonic sterile injection solutions, which can contain anti-oxidants, buffers, bacteriostats, and solutes that render the formulation compatible with the blood of the intended recipient, and aqueous and non-aqueous sterile suspensions that can include suspending agents, solubilizers, thickening agents, stabilizers, and preservatives. The formulations can be presented in unit-dose or multi-dose sealed containers, such as ampules and vials, and can be stored in a freeze-dried (lyophilized) condition requiring only the addition of the sterile liquid excipient, for example, water, for injections, immediately prior to use.

In some embodiments, the composition is a solid formulation. For example, the solid formulation can be produced in a uniform manner by lyophilization. A skilled artisan would recognize other methods, such as rotary evaporation, that can also produce solid formulations. In some embodiments, the pH of the solid formulation is neutral (e.g., pH of the composition is from about 4 to about 10, from about 5 to about 9.5, from about 5.5 to about 9, from about 6 to about 9.5, or from about 7 to about 9.5).

In some embodiments, the composition is an aqueous formulation. In some embodiments, the aqueous formulation is substantially free of solvent other than water. In some embodiments, the aqueous formulation is free of solvent other than water. In some embodiments, the pH of the aqueous formulation (e.g., clear aqueous solution) is neutral (e.g., pH of the composition is from about 4 to about 10, from about 5 to about 9.5, from about 5.5 to about 9, from about 6 to about 9.5, or from about 7 to about 9.5).

As used herein, "substantially free of solvent," in reference to an aqueous solution, refers to an aqueous solution that contains less than 0.5%, by weight, of any non-water solvent. In some embodiments, the aqueous solution contains less than 0.1%, by weight, of any non-water solvent. In some embodiments, the aqueous solution contains less than 0.05%, by weight, of any non-water solvent. In some embodiments, the aqueous solution contains less than 0.01%, by weight, of any non-water solvent.

In some embodiments, the aqueous formulation can be substantially free of a surfactant selected from the group consisting of CREMOPHOR® surfactants and Polysorbate 80. In some embodiments, the aqueous formulation can be free of a surfactant selected from the group consisting of CREMOPHOR® surfactants and Polysorbate 80.

As used herein, the term "substantially free of surfactant" refers to a formulation containing less than 0.0005%, less than 0.0003%, or less than 0.0001% of a surfactant selected from the group consisting of CREMOPHOR® surfactants and Polysorbate 80.

In some embodiments, the aqueous formulation is a clear aqueous solution. For example, the formulation can be a clear and stable aqueous solution reconstituted from a sterile lyophilized powder. In some embodiments, the aqueous formulation is a clear aqueous solution, wherein the aqueous formulation is substantially free of solvent other than water. In some embodiments, the aqueous formulation is a clear aqueous solution, wherein the aqueous formulation is free of solvent other than water.

As used herein, the term "clear aqueous solution" refers to an aqueous solution containing Cabazitaxel and HSA that is transparent and optically clear upon visual observation and essentially free of visible particles or precipitation of undissolved Cabazitaxel.

The term "essentially free of visible particles or precipitation of undissolved Cabazitaxel" can be assessed as follows: after a clear aqueous solution is filtered with a 0.22 micron filter, the amount of Cabazitaxel in the filtered aqueous solution is at least 95% of the total amount of Cabazitaxel in the aqueous solution before filtration. The total amount of Cabazitaxel in the aqueous solution before filtration includes the particles or precipitation of undissolved Cabazitaxel in the aqueous solution or with the aqueous solution. The amount of the Cabazitaxel in an aqueous solution can be measured by the methods using HPLC. The methods of measuring the amount of the Cabazitaxel in an aqueous solution are illustrated in the experimental examples described herein. The methods are commonly understood by one of ordinary skill in the art to which this disclosure belongs.

When visually observed, for example, the term "clear aqueous solution" excludes a milky aqueous solution. Further, the term "clear aqueous solution" excludes a cloudy or hazy aqueous solution.

As used herein, the term "micron" refers to a unit of measure of one one-thousandth of a millimeter. In some embodiments, the term "micron" refers to a micrometer.

As used herein, the term "aqueous solution" refers to a solution, wherein at least one solvent is water and the weight % of water in the mixture of solvents is at least 50%, at least 60%, at least 70%, or at least 90%. In some embodiments, aqueous solution is a solution in which water is the only solvent.

As used herein, the term "aqueous solvent" refers to a liquid comprising at least 50%, at least 60%, at least 70%, at least 90% or at least 95% water. In some embodiments, aqueous solvent is water.

In some embodiments, the aqueous formulation is a clear aqueous solution reconstituted from the solid formulation (e.g. the sterile lyophilized powder) in water. In some embodiments, the aqueous formulation is a clear aqueous solution reconstituted from the solid formulation (e.g. the sterile lyophilized powder) in 0.9% saline solution. In some embodiments, the aqueous formulation is a clear aqueous solution reconstituted from the solid formulation (e.g. the sterile lyophilized powder) in 5% dextrose water solution.

In some embodiments, the aqueous formulation is a clear aqueous solution reconstituted from the solid formulation (e.g. the sterile lyophilized powder) in an aqueous solvent, wherein the aqueous formulation has pH value from about 4 to about 10. In some embodiments, the aqueous formulation is a clear aqueous solution reconstituted from the solid formulation (e.g. the sterile lyophilized powder) in water, wherein the aqueous formulation has pH value from about 4 to about 10. In some embodiments, the aqueous formulation is a clear aqueous solution reconstituted from the solid formulation (e.g. the sterile lyophilized powder) in 0.9% saline solution, wherein the aqueous formulation has pH value from about 4 to about 10. In some embodiments, the aqueous formulation is a clear aqueous solution reconstituted from the solid formulation (e.g. the sterile lyophilized powder) in 5% dextrose water solution, wherein the aqueous formulation has pH value from about 4 to about 10.

In some embodiments, the aqueous formulation is a clear aqueous solution reconstituted from the solid formulation (e.g. the sterile lyophilized powder) in an aqueous solvent, wherein the aqueous formulation has pH value from about 5 to about 9.5. In some embodiments, the aqueous formulation is a clear aqueous solution reconstituted from the solid formulation (e.g. the sterile lyophilized powder) in water, wherein the aqueous formulation has pH value from about 5 to about 9.5. In some embodiments, the aqueous formulation is a clear aqueous solution reconstituted from the solid formulation (e.g. the sterile lyophilized powder) in 0.9% saline solution, wherein the aqueous formulation has pH value from about 5 to about 9.5. In some embodiments, the aqueous formulation is a clear aqueous solution reconstituted from the solid formulation (e.g. the sterile lyophilized powder) in 5% dextrose water solution, wherein the aqueous formulation has pH value from about 5 to about 9.5.

In some aspects of the aforementioned embodiments, the concentration of the reconstituted solid (e.g., the sterile lyophilized powder comprising Cabazitaxel, HSA, and arginine) in the aqueous formulation is about 10 mg, about 15 mg, about 20 mg, about 25 mg, about 30 mg, about 35 mg, about 40 mg, about 45 mg, about 50 mg, about 55 mg, about 60 mg, about 65 mg, about 70 mg, about 75 mg, about 80 mg, about 100 mg, or about 150 mg per 1 ml of the aqueous solvent. In some aspects of the aforementioned embodiments, the concentration of the reconstituted solid (e.g., the sterile lyophilized powder comprising Cabazitaxel, HSA, and arginine) in the aqueous formulation is from about 10 mg per 1 ml to about 250 mg per 1 ml of the aqueous solvent. In some aspects of the aforementioned embodiments, the concentration of the reconstituted solid (e.g., the sterile lyophilized powder comprising Cabazitaxel, HSA, and arginine) in the aqueous formulation is from about 15 mg per 1 ml to about 100 mg per 1 ml of the aqueous solvent. In some aspects of the aforementioned embodiments, the concentration of the reconstituted solid (e.g., the sterile lyophilized powder comprising Cabazitaxel, HSA, and arginine) in the aqueous formulation is from about 20 mg per 1 ml to about 50 mg per 1 ml of the aqueous solvent. In some aspects of the aforementioned embodiments, the concentration of the reconstituted solid (e.g., the sterile lyophilized powder comprising Cabazitaxel, HSA, and arginine) in the aqueous formulation is from about 25 mg per 1 ml to about 45 mg per 1 ml of the aqueous solvent.

In some embodiments, the aqueous formulation has pH value from about 4 to about 10. In some embodiments, the aqueous formulation has pH value from about 5 to about 9. In some embodiments, the aqueous formulation has pH value from about 5 to about 9.5. In some embodiments, the aqueous formulation has pH value from about 6 to about 9.5. In some embodiments, the aqueous formulation has pH value from about 7 to about 9.5. In some embodiments, the aqueous formulation has pH value from about 7 to about 9. In some embodiments, the aqueous formulation has pH value from about 8 to about 9.5. In some embodiments, the aqueous formulation has pH value from about 6 to about 9. In some embodiments, the aqueous formulation has pH value from about 7 to about 9. In some embodiments, the aqueous formulation is substantially free of solvent other than water. In some embodiments, the aqueous formulation is free of solvent other than water.

In some embodiments, the aqueous formulation is a clear aqueous solution, wherein the aqueous formulation has pH value from about 4 to about 10, and wherein the aqueous formulation is substantially free of solvent other than water. In some embodiments, the aqueous formulation is a clear aqueous solution, wherein the aqueous formulation has pH value from about 4 to about 10, and wherein the aqueous formulation is free of solvent other than water. In some embodiments, the aqueous formulation is a clear aqueous solution, wherein the aqueous formulation has pH value from about 5 to about 9.5, and wherein the aqueous formulation is substantially free of solvent other than water. In some embodiments, the aqueous formulation is a clear aqueous solution, wherein the aqueous formulation has pH value from about 5 to about 9.5, and wherein the aqueous formulation is free of solvent other than water.

In some embodiments, after a clear aqueous solution is filtered by a 0.22 micron filter, the amount of Cabazitaxel in the filtered aqueous solution is at least 96% of the total amount of Cabazitaxel in the aqueous solution before filtration. In some embodiments, after a clear aqueous solution is filtered by a 0.22 micron filter, the amount of Cabazitaxel in the filtered aqueous solution is at least 97% of the total amount of Cabazitaxel in the aqueous solution before filtration. In some embodiments, after a clear aqueous solution is filtered by a 0.22 micron filter, the amount of Cabazitaxel in the filtered aqueous solution is at least 98% of the total amount of Cabazitaxel in the aqueous solution before filtration. In some embodiments, after a clear aqueous solution is filtered by a 0.22 micron filter, the amount of Cabazitaxel in the filtered aqueous solution is at least 99% of the total amount of Cabazitaxel in the aqueous solution before filtration. In some embodiments, after a clear aqueous solution is filtered by a 0.22 micron filter, the amount of Cabazitaxel in the filtered aqueous solution is at least 99.5% of the total amount of Cabazitaxel in the aqueous solution before filtration. In some embodiments, the aqueous formulation is substantially free of solvent other than water. In some embodiments, the aqueous formulation is free of solvent other than water.

In some embodiments, after the aqueous formulation (e.g. a clear aqueous solution) is filtered by a 0.22 micron filter, the amount of Cabazitaxel in the filtered aqueous solution is at least 96%, 97%, 98%, 99%, or 99.5% of the total amount of Cabazitaxel in the aqueous solution before filtration, wherein the clear aqueous solution has pH value from about 5 to about 8, and wherein the clear aqueous solution is substantially free of solvent other than water. In some embodiments, after the aqueous formulation (e.g. a clear aqueous solution) is filtered by a 0.22 micron filter, the amount of Cabazitaxel in the filtered aqueous solution is at least 96%, 97%, 98%, 99%, or 99.5% of the total amount of Cabazitaxel in the aqueous solution before filtration, wherein the clear aqueous solution has pH value from about 5.5 to about 7, and wherein the clear aqueous solution is substantially free of solvent other than water.

In some embodiments, the aqueous formulation is a clear aqueous solution for at least 1 hour, 2 hours, 3 hours, 4 hours, 5 hours, 6 hours, 7 hours, 8 hours, 10 hours, 12 hours, 24 hours, 72 hours, one week, or one month. In some embodiments, the aqueous formulation is a clear aqueous solution for at least 2 hours. In some embodiments, the aqueous formulation is a clear aqueous solution for at least 4 hours. In some embodiments, the aqueous formulation is a clear aqueous solution for at least 6 hours. In some embodiments, the aqueous formulation is a clear aqueous solution for at least 8 hours. In some embodiments, the aqueous formulation is a clear aqueous solution for at least 24 hours. In some embodiments, the aqueous formulation is a clear aqueous solution for at least 1 hour, 2 hours, 3 hours, 4 hours, 5 hours, 6 hours, 7 hours, 8 hours, 10 hours, 12 hours, or 24 hours at a temperature from about 10° C. to about 35° C. In some embodiments, the aqueous formulation is a clear aqueous solution for at least 1 hour, 2 hours, 3 hours, 4 hours, 5 hours, 6 hours, 7 hours, 8 hours, 10 hours, 12 hours, 24 hours, 72 hours, one week, or one month at a temperature from about 1° C. to about 10° C. In some embodiments, the aqueous formulation is a clear aqueous solution for at least 6 hours at a temperature from about 1° C. to about 10° C. In some embodiments, the aqueous formulation is a clear aqueous solution for at least 24 hours at a temperature from about 1° C. to about 10° C. In some embodiments, the aqueous formulation is a clear aqueous solution for at least 72 hours at a temperature from about 1° C. to about 10° C. In some embodiments, the aqueous formulation is substantially free of solvent other than water. In some embodiments, the aqueous formulation is free of solvent other than water.

In some embodiments, the aqueous formulation is a clear aqueous solution for at least 4 hours at a temperature from about 1° C. to about 35° C., about 1° C. to about 10° C., about 10° C. to about 20° C., about 20° C. to about 25° C., or about 1° C., about 5° C., about 10° C., about 15° C., about 20° C., about 25° C., or about 30° C. In some embodiments, the aqueous formulation is a clear aqueous solution for at least 8 hours at a temperature from about 1° C. to about 35° C., about 1° C. to about 10° C., about 10° C. to about 20° C., about 20° C. to about 25° C., or about 1° C., about 5° C., about 10° C., about 15° C., about 20° C., about 25° C., or about 30° C. In some embodiments, the aqueous formulation is a clear aqueous solution for at least 24 hours at a temperature from about 1° C. to about 35° C., about 1° C. to about 10° C., about 10° C. to about 20° C., about 20° C. to about 25° C., or about 1° C., about 5° C., about 10° C., about 15° C., about 20° C., about 25° C., or about 30° C. In some embodiments, the aqueous formulation is substantially free of solvent other than water. In some embodiments, the aqueous formulation is free of solvent other than water.

In some embodiments, the concentration of Cabazitaxel in the aqueous formulation is from about 0.01 mg per 1 ml to about 1 mg per 1 ml of the aqueous solvent. In some embodiments, the concentration of Cabazitaxel in the aqueous formulation is from about 0.02 mg per 1 ml to about 0.5 mg per 1 ml of the aqueous solvent. In some embodiments, the concentration of Cabazitaxel in the aqueous formulation is from about 0.03 mg per 1 ml to about 0.3 mg per 1 ml of the aqueous solvent. In some embodiments, the concentration of Cabazitaxel in the aqueous formulation is from about 0.05 mg per 1 ml to about 0.2 mg per 1 ml of the aqueous solvent. In some embodiments, the concentration of Cabazitaxel in the aqueous formulation is from about 0.07 mg per 1 ml to about 0.15 mg per 1 ml of the aqueous solvent. In some embodiments, the concentration of Cabazitaxel in the aqueous formulation is from about 0.08 mg per 1 ml to about 0.12 mg per 1 ml of the aqueous solvent. In some embodiments, the concentration of Cabazitaxel in the aqueous formulation is about 0.08 mg per 1 ml of the aqueous solvent. In some embodiments, the concentration of Cabazitaxel in the aqueous formulation is about 0.09 mg per 1 ml of the aqueous solvent. In some embodiments, the concentration of Cabazitaxel in the aqueous formulation is about 0.1 mg per 1 ml of the aqueous solvent. In some embodiments, the concentration of Cabazitaxel in the aqueous formulation is about 0.11 mg per 1 ml of the aqueous solvent. In some embodiments, the concentration of Cabazitaxel in the aqueous formulation is about 0.12 mg per 1 ml of the aqueous solvent. In some embodiments, the concentration of Cabazitaxel in the aqueous formulation is about 0.15 mg per 1 ml of the aqueous solvent. In some embodiments, the aqueous formulation is substantially free of solvent other than water. In some embodiments, the aqueous formulation is free of solvent other than water.

In some embodiments, the aqueous formulation is a clear aqueous solution, wherein the concentration of Cabazitaxel in the aqueous formulation is from about 0.01 mg per 1 ml to about 1 mg per 1 ml of the aqueous solvent. In some embodiments, the aqueous formulation is a clear aqueous solution, wherein the concentration of Cabazitaxel in the aqueous formulation is from about 0.02 mg per 1 ml to about 0.5 mg per 1 ml of the aqueous solvent. In some embodiments, the aqueous formulation is a clear aqueous solution, wherein the concentration of Cabazitaxel in the aqueous formulation is from about 0.05 mg per 1 ml to about 0.3 mg per 1 ml of the aqueous solvent. In some embodiments, the aqueous formulation is a clear aqueous solution, wherein the concentration of Cabazitaxel in the aqueous formulation is from about 0.07 mg per 1 ml to about 0.15 mg per 1 ml of the aqueous solvent. In some embodiments, the aqueous formulation is a clear aqueous solution, wherein the concentration of Cabazitaxel in the aqueous formulation is from about 0.08 mg per 1 ml to about 0.12 mg per 1 ml of the aqueous solvent. In some embodiments, the aqueous formulation is a clear aqueous solution, wherein the concentration of Cabazitaxel in the aqueous formulation is about 0.1 mg per 1 ml of the aqueous solvent. In some embodiments, the aqueous formulation is substantially free of solvent other than water. In some embodiments, the aqueous formulation is free of solvent other than water.

In some embodiments, the aqueous formulation is a clear aqueous solution, wherein the concentration of Cabazitaxel in the aqueous formulation is from about 0.01 mg per 1 ml to about 1 mg per 1 ml of the aqueous solvent, and wherein the aqueous formulation is substantially free of solvent other than water. In some embodiments, the aqueous formulation is a clear aqueous solution, wherein the concentration of Cabazitaxel in the aqueous formulation is from about 0.02 mg per 1 ml to about 0.5 mg per 1 ml of the aqueous solvent, and wherein the aqueous formulation is substantially free of solvent other than water. In some embodiments, the aqueous formulation is a clear aqueous solution, wherein the concentration of Cabazitaxel in the aqueous formulation is from about 0.05 mg per 1 ml to about 0.3 mg per 1 ml of the aqueous solvent, and wherein the aqueous formulation is substantially free of solvent other than water. In some embodiments, the aqueous formulation is a clear aqueous solution, wherein the concentration of Cabazitaxel in the aqueous formulation is from about 0.07 mg per 1 ml to about 0.15 mg per 1 ml of the aqueous solvent, and wherein the aqueous formulation is substantially free of solvent other than water. In some embodiments, the aqueous formulation is a clear aqueous solution, wherein the concentration of Cabazitaxel in the aqueous formulation is about 0.1 mg per 1 ml of the aqueous solvent, and wherein the aqueous formulation is substantially free of solvent other than water.

Also, provided herein is a pharmaceutical composition comprising the composition comprising Cabazitaxel, human serum albumin, and arginine as described herein, and a pharmaceutically acceptable carrier.

In some embodiments, the pharmaceutical composition further comprises at least one anti-cancer drug (e.g., any one of the anti-cancer drugs as described herein). In some embodiments, the pharmaceutical composition further comprises a stabilizer selected from sodium caprylate and sodium N-acetyltryptophanate.

As used herein, the term "pharmaceutically acceptable carrier" is meant any solution used to solubilize and deliver an agent to a subject. A desirable pharmaceutically acceptable carrier is saline or water. Other pharmaceutically acceptable carrier and their formulation are known to one skilled in the art and described, for example, in Remington's Pharmaceutical Sciences. (20$^{th}$ edition), ed. A. Gennaro, 2003, Lippincon Williams & Wilkins.

Pharmaceutically acceptable carriers that may be used in the pharmaceutical compositions of the present application include, but are not limited to, ion exchangers, alumina, aluminum stearate, lecithin, serum proteins (other than HSA), buffer substances such as phosphates, glycine, sorbic acid, potassium sorbate, salts or electrolytes, such as protamine sulfate, disodium hydrogen phosphate, potassium hydrogen phosphate, sodium chloride, zinc salts, colloidal silica, magnesium trisilicate, and cellulose-based substances.

In some embodiments, the pharmaceutical composition is free of a surfactant selected from the group consisting of CREMOPHOR® surfactants and Polysorbate 80. In some embodiments, the pharmaceutical composition is substantially free of a surfactant selected from the group consisting of CREMOPHOR® surfactants and Polysorbate 80.

Also, provided herein is a method of treating a cancer (e.g., any one of cancers described herein), the method comprising the step of administering to a subject in need thereof a therapeutically effective amount of a pharmaceutical composition comprising the composition comprising Cabazitaxel, human serum albumin, and arginine as described herein, and a pharmaceutically acceptable carrier.

As used herein, the terms "individual", "patient", or "subject" are used interchangeably and refer to any animal, including mammals, preferably mice, rats, other rodents, rabbits, dogs, cats, swine, cattle, sheep, horses, or primates, and most preferably humans.

In some embodiments, the cancer is selected from the group consisting of bladder cancer, brain cancer, breast cancer, colorectal cancer, cervical cancer, gastrointestinal cancer, genitourinary cancer, head and neck cancer, lung cancer, ovarian cancer, pancreatic cancer, prostate cancer, renal cancer, skin cancer, and testicular cancer.

In some embodiments, cancer is selected from sarcoma, angiosarcoma, fibrosarcoma, rhabdomyosarcoma, liposarcoma, myxoma, rhabdomyoma, fibroma, lipoma, teratoma, non-small cell lung cancer (NSCLC), bronchogenic carcinoma squamous cell, undifferentiated small cell, undifferentiated large cell, adenocarcinoma, alveolar bronchiolar carcinoma, bronchial adenoma, sarcoma, lymphoma, chondromatous hamartoma, mesothelioma, gastrointestinal cancer, cancer of the esophagus, squamous cell carcinoma, adenocarcinoma, leiomyosarcoma, lymphoma, cancer of the stomach, carcinoma, lymphoma, leiomyosarcoma, cancer of the pancreas, ductal adenocarcinoma, insulinoma, glucagonoma, gastrinoma, carcinoid tumor, vipoma, cancer of the small bowel, adenocarcinoma, lymphoma, carcinoid tumors, Kaposi's sarcoma, leiomyoma, hemangioma, lipoma, neurofibroma, fibroma, cancer of the large bowel or colon, tubular adenoma, villous adenoma, hamartoma, leiomyoma, genitourinary tract cancer, cancer of the kidney adenocarcinoma, Wilm's tumor (nephroblastoma), lymphoma, leukemia, cancer of the bladder, cancer of the urethra, squamous cell carcinoma, transitional cell carcinoma, cancer of the prostate, cancer of the testis, seminoma, teratoma, embryonal carcinoma, teratocarcinoma, choriocarcinoma, sarcoma, interstitial cell carcinoma, fibroma, fibroadenoma, adenomatoid tumors, lipoma, liver cancer, hepatoma hepatocellular carcinoma, cholangiocarcinoma, hepatoblastoma, angiosarcoma, hepatocellular adenoma, hemangioma, bone cancer, osteogenic sarcoma (osteosarcoma), fibrosarcoma, malignant fibrous histiocytoma, chondrosarcoma, Ewing's sarcoma, malignant lymphoma (reticulum cell sarcoma), multiple myeloma, malignant giant cell tumor, chordoma, osteochrondroma (osteocartilaginous exostoses), benign chondroma, chondroblastoma, chondromyxofibroma, osteoid osteoma giant cell tumor, nervous system cancer, cancer of the skull, osteoma, hemangioma, granuloma, xanthoma, osteitis deformans, cancer of the meninges meningioma, meningiosarcoma, gliomatosis, cancer of the brain, astrocytoma, medulloblastoma, glioma, ependymoma, germinoma (pinealoma), glioblastoma multiforme, oligodendroglioma, schwannoma, retinoblastoma, congenital tumors, cancer of the spinal cord, neurofibroma, meningioma, glioma, sarcoma, gynecological cancer, cancer of the uterus, endometrial carcinoma, cancer of the cervix, cervical carcinoma, pre tumor cervical dysplasia, cancer of the ovaries, ovarian carcinoma, serous cystadenocarcinoma, mucinous cystadenocarcinoma, unclassified carcinoma, granulosa-theca cell tumor, Sertoli Leydig cell tumor, dysgerminoma, malignant teratoma, cancer of the vulva, squamous cell carcinoma, intraepithelial carcinoma, adenocarcinoma, fibrosarcoma, melanoma, cancer of the vagina, clear cell carcinoma, squamous cell carcinoma, botryoid sarcoma, embryonal rhabdomyosarcoma, cancer of the fallopian tubes, hematologic cancer, cancer of the blood, acute myeloid leukemia (AML), chronic myeloid leukemia (CML), acute lymphoblastic leukemia (ALL), chronic lymphoblastic leukemia, chronic lymphocytic leukemia, myeloproliferative diseases, multiple myeloma, myelodysplastic syndrome, Hodgkin's lymphoma, non-Hodgkin's lymphoma (malignant lymphoma), Waldenstrom's macroglobulinemia, skin cancer, malignant melanoma, basal cell carcinoma, squamous cell carcinoma, Kaposi's sarcoma, moles dysplastic nevi, lipoma, angioma, dermatofibroma, keloids, psoriasis, adrenal gland cancer, and neuroblastoma.

As used herein, an "effective amount," "therapeutically effective amount," or a "pharmaceutically-effective amount" in reference to the compounds or compositions of the instant invention refers to the amount sufficient to induce a desired biological, pharmacological, or therapeutic outcome in a subject. That result can be reduction, mitigation, delay, shortening the time to resolution of, alleviation of the signs or symptoms of, or exert a medically-beneficial effect upon the underlying pathophysiology or pathogenesis of an expected or observed side-effect, toxicity, disorder or condition, or any other desired alteration of a biological system. In cancer treatment, the result will generally include the reduction, mitigation, limitation, and/or, delay of the deleterious physiological manifestations, growth or metastases of neoplasms.

In some embodiments, the cancer is a solid tumor cancer. In some embodiments, the cancer is a prostate cancer.

In some embodiments, the method of treating a prostate cancer comprises the step of administering to a subject in need thereof of a therapeutically effective amount of a pharmaceutical composition comprising the composition comprising Cabazitaxel, human serum albumin, and arginine as described herein, prednisone, and a pharmaceutically acceptable carrier.

In some embodiments, the method of treating cancer (e.g. any one of cancers described herein) comprises the step of administering to a subject in need thereof of a therapeutically effective amount of a composition comprising the composition comprising Cabazitaxel, human serum albumin, and arginine as described herein, and a therapeutically effective amount of at least one inhibitor of the following kinases for the treatment of cancer: PIM, Akt1, Akt2, Akt3, TGF-βR, PKA, PKG, PKC, CaM-kinase, phosphorylase kinase, MEKK, ERK, MAPK, mTOR, EGFR, HER2, HER3, HER4, INS-R, IGF-1R, IR-R, PDGFαR, PDGFβR, CSFIR, KIT, FLK-II, KDR/FLK-1, FLK-4, fit-1, FGFR1, FGFR2, FGFR3, FGFR4, c-Met, Ron, Sea, TRKA, TRKB, TRKC, FLT3, VEGFR/Flt2, Flt4, EphA1, EphA2, EphA3, EphB2, EphB4, Tie2, Src, Fyn, Lck, Fgr, Btk, Fak, SYK, FRK, JAK, ABL, ALK and B-Raf.

In some embodiments, the method of treating cancer (e.g. any one of cancers described herein) comprises the step of administering to a subject in need thereof of a therapeutically effective amount of a pharmaceutical composition comprising the composition comprising Cabazitaxel, human serum albumin, and arginine as described herein, and a therapeutically effective amount of at least one anti-cancer drug. Examples of an anti-cancer drug include aberaterone, aberaterone acetate, abarelix, aldesleukin, alemtuzumab, alitretinoin, allopurinol, altretamine, anastrozole, arsenic trioxide, asparaginase, azacitidine, bavituximab, bevacizumab, bexarotene, bleomycin, bortezombi, bortezomib, busulfan intravenous, busulfan oral, calusterone, capecitabine, carboplatin, carmustine, cetuximab, chlorambucil, cisplatin, cladribine, clofarabine, cyclophosphamide, cytarabine, dacarbazine, dactinomycin, dalteparin sodium, dasatinib, daunorubicin, decitabine, denileukin, denileukin diftitox, dexrazoxane, cabazitaxel, doxorubicin, dromostanolone propionate, eculizumab, enzalutamide, epirubicin, erlotinib, estramustine, etoposide phosphate, etoposide, exemestane, fentanyl citrate, filgrastim, floxuridine, fludarabine, fluorouracil, fulvestrant, gefitinib, gemcitabine, gemtuzumab ozogamicin, goserelin acetate, histrelin acetate, ibritumomab tiuxetan, idarubicin, ifosfamide, imatinib mesylate, interferon alfa 2a, irinotecan, lapatinib ditosylate, lenalidomide, letrozole, leucovorin, leuprolide acetate, levamisole, lomustine, meclorethamine, megestrol acetate, melphalan, mercaptopurine, methotrexate, methoxsalen, mitomycin C, mitotane, mitoxantrone, nandrolone phenpropionate, nelarabine, nofetumomab, oxaliplatin, paclitaxel, pamidronate, panitumumab, pegaspargase, pegfilgrastim, pemetrexed disodium, pentostatin, pipobroman, plicamycin, procarbazine, quinacrine, rasburicase, rituximab, ruxolitinib, sorafenib, streptozocin, sunitinib, sunitinib maleate, tamoxifen, temozolomide, teniposide, testolactone, thalidomide, thioguanine, thiotepa, topotecan, toremifene, tositumomab, trastuzumab, tretinoin, uracil mustard, valrubicin, vinblastine, vincristine, vinorelbine, vorinostat and zoledronate.

In some embodiments, a composition comprising the composition comprising a Cabazitaxel, human serum albumin, and arginine as described herein and an anti-cancer drug are administered simultaneously.

In some embodiments, a composition comprising the composition comprising Cabazitaxel, human serum albumin, and arginine as described herein and an anti-cancer drug are administered consecutively.

The composition comprising Cabazitaxel, human serum albumin, and arginine described herein can be administered to an individual, such as human, via various routes, such as parenterally, including intravenous, intra-arterial, intraperitoneal, intrapulmonary, oral, inhalation, intravesicular, intramuscular, intra-tracheal, subcutaneous, intraocular, intrathecal, or transdermal. For example, the composition can be administered by inhalation to treat conditions of the respiratory tract. The composition can be used to treat respiratory conditions such as pulmonary fibrosis, broncheolitis obliterans, lung cancer, bronchoalveolar carcinoma, and the like. In some embodiments, the composition described herein is administrated intravenously.

The methods described herein may be performed alone or in conjunction with another therapy, such as surgery, radiation, chemotherapy, immunotherapy, gene therapy, and the like. Additionally, a person having a greater risk of developing the proliferative disease may receive treatments to inhibit and/or delay the development of the disease.

As will be understood by those of ordinary skill in the art, the appropriate doses of cabazitaxel will be approximately those already employed in clinical therapies wherein cabazitaxel is administered alone or in combination with other chemotherapeutic agents. Variation in dosage will likely occur depending on the condition being treated. Appropriate effective doses will also vary, as recognized by those skilled in the art, depending on the severity of the disease, the route of administration, the sex, age and general health condition of the subject, excipient usage, the possibility of co-usage with other therapeutic treatments such as use of other agents, and the judgment of the treating physician. For example, guidance for selecting an effective dose can be determined by reference to the prescribing information for cabazitaxel.

Also, provided herein is a liquid composition comprising Cabazitaxel and human serum albumin, wherein the human serum albumin and the Cabazitaxel in the composition have a ratio by weight of no less than 120:1, wherein arginine and the Cabazitaxel in the composition have a ratio by weight of no less than 1:1, and wherein the composition comprises water, t-butanol, and ethanol. In some embodiments, the liquid composition is a clear aqueous solution.

In some embodiments, the human serum albumin and the Cabazitaxel in the composition have a ratio by weight of no less than about 150:1. In some embodiments, the human serum albumin and the Cabazitaxel in the composition have a ratio by weight of no less than about 200:1. In some embodiments, the human serum albumin and the Cabazitaxel in the composition have a ratio by weight of no less than about 250:1. In some embodiments, the human serum albumin and the Cabazitaxel in the composition have a ratio by weight of no less than about 300:1. In some embodiments, the Cabazitaxel and the human serum albumin in the composition are in a ratio by weight from about 1:250 to about 1:600. In some embodiments, the Cabazitaxel and the human serum albumin in the composition are in a ratio by weight from about 1:250 to about 1:400. In some embodiments, the Cabazitaxel and the human serum albumin in the composition are in a ratio by weight from about 1:300 to about 1:500. In some embodiments, the Cabazitaxel and the human serum albumin in the composition are in a ratio by weight from about 1:300 to about 1:400. In some embodiments, the Cabazitaxel and the human serum albumin in the composition are in a ratio by weight from about 1:320 to about 1:450. In some embodiments, the Cabazitaxel and the human serum albumin in the composition are in a ratio by weight from about 1:320 to about 1:400. In some embodiments, the Cabazitaxel and the human serum albumin in the composition are in a ratio by weight from about 1:320 to about 1:380. In some embodiments, the Cabazitaxel and the human serum albumin in the composition are in a ratio by weight of about 1:300, about 1:310, about 1:320, about 1:330, about 1:340, about 1:350, about 1:360, about 1:370, about 1:380, about 1:390, or about 1:400.

In some embodiments, arginine and Cabazitaxel in the composition have a ratio by weight of no less than about 2:1. In some embodiments, arginine and Cabazitaxel in the composition have a ratio by weight of no less than about 3:1. In some embodiments, arginine and Cabazitaxel in the composition have a ratio by weight of no less than about 5:1. In some embodiments, arginine and Cabazitaxel in the composition have a ratio by weight of no less than about 10:1. In some embodiments, arginine and Cabazitaxel in the composition have a ratio by weight of no less than about 15:1.

In some embodiments, arginine and Cabazitaxel in the composition have a ratio by weight from about 1:1 to about 200:1. In some embodiments, arginine and Cabazitaxel in the composition have a ratio by weight from about 10:1 to about 200:1. In some embodiments, arginine and Cabazitaxel in the composition have a ratio by weight from about 15:1 to about 200:1. In some embodiments, arginine and Cabazitaxel in the composition have a ratio by weight from about 1:1 to about 150:1. In some embodiments, arginine and Cabazitaxel in the composition have a ratio by weight from about 1:1 to about 100:1. In some embodiments, arginine and Cabazitaxel in the composition have a ratio by weight from about 5:1 to about 150:1. In some embodiments, arginine and Cabazitaxel in the composition have a ratio by weight from about 5:1 to about 100:1. In some embodiments, arginine and Cabazitaxel in the composition have a ratio by weight from about 15:1 to about 150:1. In some embodiments, arginine and Cabazitaxel in the composition have a ratio by weight from about 15:1 to about 100:1. In some embodiments, arginine and Cabazitaxel in the composition have a ratio by weight from about 2:1 to about 50:1. In some embodiments, arginine and Cabazitaxel in the composition have a ratio by weight from about 3:1 to about 30:1. In some embodiments, arginine and Cabazitaxel in the composition have a ratio by weight from about 5:1 to about 25:1.

In some embodiments, after the composition is filtered by a 0.22 micron filter, the amount of Cabazitaxel in the filtered aqueous solution is at least 95% of the total amount of Cabazitaxel in the liquid composition before filtration. In some embodiments, after the composition is filtered by a 0.22 micron filter, the amount of Cabazitaxel in the filtered aqueous solution is at least 96% of the total amount of Cabazitaxel in the liquid composition before filtration. In some embodiments, after the composition is filtered by a 0.22 micron filter, the amount of Cabazitaxel in the filtered aqueous solution is at least 97% of the total amount of Cabazitaxel in the liquid composition before filtration. In some embodiments, after the composition is filtered by a 0.22 micron filter, the amount of Cabazitaxel in the filtered aqueous solution is at least 98% of the total amount of Cabazitaxel in the liquid composition before filtration. In some embodiments, after the composition is filtered by a 0.22 micron filter, the amount of Cabazitaxel in the filtered aqueous solution is at least 99% of the total amount of Cabazitaxel in the liquid composition before filtration.

In some embodiments, the liquid composition is a clear aqueous solution for at least 1 hour, 2 hours, 3 hours, 4 hours, 5 hours, 6 hours, or 8 hours. In some embodiments, the liquid composition is a clear aqueous solution for at least 1 hour. In some embodiments, the liquid composition is a clear aqueous solution for at least 2 hours. In some embodiments, the liquid composition is a clear aqueous solution for at least 3 hours. In some embodiments, the liquid composition is a clear aqueous solution for at least 6 hours.

In some embodiments, the aqueous formulation has pH value from about 4 to about 10. In some embodiments, the aqueous formulation has pH value from about 5 to about 9. In some embodiments, the aqueous formulation has pH value from about 6 to about 9. In some embodiments, the aqueous formulation has pH value from about 7 to about 9.

Kits

The present invention also includes pharmaceutical kits useful, for example, in the treatment or prevention of any one of diseases or disorders referred to herein, which include one or more containers containing a pharmaceutical composition comprising a composition of Cabazitaxel, the human serum albumin, and arginine as described herein. Such kits can further include, if desired, one or more of various conventional pharmaceutical kit components, such as, for example, containers with one or more pharmaceutically acceptable carriers (e.g., water, 0.9% saline, or 5% dextrose), additional containers, etc., as will be readily apparent to those skilled in the art. Instructions, either as inserts or as labels, indicating quantities of the components to be administered (e.g., dosage amounts as described herein), guidelines for administration, and/or guidelines for mixing the components, can also be included in the kit.

Methods of Making

Also, provided herein are methods to prepare a composition comprising Cabazitaxel, human serum albumin, and arginine as described herein.

In some embodiments, the method comprises mixing an organic solution of Cabazitaxel in a polar water-miscible organic solvent and a first aqueous solution containing human serum albumin and arginine to form a second aqueous solution, wherein the second aqueous solution is a clear aqueous solution.

In some embodiments, the method further comprises removing said polar water-miscible organic solvent and water from the second aqueous solution.

A non-limiting preferred method is as follows.

Formation of the Organic Solution

In some embodiments, Cabazitaxel is dissolved in a polar organic solvent (e.g., an alcohol such as methanol, ethanol, t-butanol, and/or isopropanol; acetone, THF, $CH_3CN$; DMF; or mixtures thereof) to form an organic solution.

As used herein, the term "organic solution" refers to a solution wherein at least one solvent is a non-aqueous solvent and the weight % of the non-aqueous solvent in the mixture of solvents is at least 50%, at least 60%, at least 70% or at least 90%. In some embodiments, organic solution is a solution in which does not comprise water as a solvent.

In some embodiments, the terms "organic solvent" and "non-aqueous solvent" are used interchangeably and refer to a liquid comprising is at least 50%, at least 60%, at least 70%, at least 90%, or at least 95% of a solvent other than water.

The polar organic solvent is miscible in water. In some embodiments, the polar organic solvent is an alcohol. In some embodiments, the polar organic solvent is ethanol or t-butanol, or mixtures thereof. In some embodiments, the polar organic solvent can be acetone. In some embodiments, the polar organic solvent is a mixture of ethanol and t-butanol. In some embodiments, the polar organic solvent is a mixture of ethanol and t-butanol, in which the ratio of (v/v) ethanol and t-butanol is from about 5:1 to about 1:50. In some embodiments, the polar organic solvent is a mixture of ethanol and t-butanol, in which the ratio of (v/v) ethanol and t-butanol is from about 1:1 to about 1:30. In some embodiments, the polar organic solvent is a mixture of ethanol and t-butanol, in which the ratio of (v/v) ethanol and t-butanol is from about 1:2 to about 1:20. In some embodiments, the polar organic solvent is a mixture of ethanol and t-butanol, in which the ratio of (v/v) ethanol and t-butanol is from about 1:4 to about 1:15. In some embodiments, the polar organic solvent is a mixture of ethanol and t-butanol, in which the ratio of (v/v) ethanol and t-butanol is from about 1:6 to about 1:14. In some embodiments, the polar organic solvent is a mixture of ethanol and t-butanol, in which the ratio of (v/v) ethanol and t-butanol is about 1:9. In some embodiments, the polar organic solvent is a mixture of ethanol and t-butanol, in which the ratio of (v/v) ethanol and t-butanol is about 1:10. In some embodiments, the polar organic solvent is a mixture of ethanol and t-butanol, in which the ratio of (v/v) ethanol and t-butanol is about 1:11. In some embodiments, the polar organic solvent is a mixture of ethanol and t-butanol, in which the ratio of (v/v) ethanol and t-butanol is about 1:12. In some embodiments, the polar organic solvent is a mixture of ethanol and t-butanol, in which the ratio of (v/v) ethanol and t-butanol is about 1:13. In some embodiments, the polar organic solvent is a mixture of ethanol and t-butanol, in which the ratio of (v/v) ethanol and t-butanol is about 1:14. In some embodiments, the polar organic solvent is a mixture of ethanol and t-butanol, in which the ratio of (v/v) ethanol and t-butanol is about 1:8. In some embodiments, the polar organic solvent is a mixture of ethanol and t-butanol, in which the ratio of (v/v) ethanol and t-butanol is about 1:7. In some embodiments, the polar organic solvent is a mixture of ethanol and t-butanol, in which the ratio of (v/v) ethanol and t-butanol is about 1:6.5. In some embodiments, the polar organic solvent is a mixture of ethanol and t-butanol, in which the ratio of (v/v) ethanol and t-butanol is about 1:6.

Formation of the First Aqueous Solution

In some embodiments, the first aqueous solution comprises an intravenous Human Albumin (human serum albumin) solution for infusion (e.g. Human Albumin USP; prepared as a 5%, 20%, or 25% protein solution). In some embodiments, the first aqueous solution comprises an intravenous Human Albumin (human serum albumin) solution for infusion (e.g. Human Albumin USP; prepared as a 5%, 20%, or 25% protein solution), and arginine.

In some embodiments, the amount of aqueous solvent in the first aqueous solution is from about 0.2 mL to about 10 mL per 100 mg of human serum albumin. In some embodiments, the amount of aqueous solvent in the first aqueous solution is from about 0.4 mL to about 5 mL per 100 mg of human serum albumin. In some embodiments, the amount of aqueous solvent in the first aqueous solution is from about 0.5 mL to about 3 mL per 100 mg of human serum albumin. In some embodiments, the amount of aqueous solvent in the first aqueous solution is from about 1 mL to about 2 mL per 100 mg of human serum albumin. In some embodiments, the amount of aqueous solvent in the first aqueous solution is from about 1.2 mL to about 1.8 mL per 100 mg of human serum albumin. In some embodiments, the amount of aqueous solvent in the first aqueous solution is about 0.75 mL, about 1 mL, about 1.2 mL, about 1.3 mL, about 1.4 mL, about 1.6 mL, about 1.6 mL, about 1.7 mL, or about 2 mL per 100 mg of human serum albumin.

In some embodiments, the resulting composition comprising Cabazitaxel, human serum albumin, arginine can have any molar ratio or any ratio by weight of the Cabazitaxel to the human serum albumin as described herein.

In some embodiments, the preparation of the organic solution and the preparation of the first aqueous solution are performed concurrently.

In some embodiments, the preparation of the organic solution and the preparation of the first aqueous solution are performed sequentially. In some embodiments, the preparation of the organic solution is performed before the preparation of the first aqueous solution. In some embodiments, the preparation of the first aqueous solution is performed before the preparation of the organic solution.

In some embodiments, the range of pH in the first aqueous solution is from about 3 to about 11, from about 4 to about 10, from about 3 to about 9.

Formation of the Second Aqueous Solution

In some embodiments, the organic solution of Cabazitaxel is mixed with the first aqueous solution to form a second aqueous solution. In some embodiments, the second aqueous solution is a clear aqueous solution.

In some embodiments, the second aqueous solution comprises t-butanol. In some embodiments, the second aqueous solution comprises ethanol. In some embodiments, the second aqueous solution comprises t-butanol and ethanol. In some embodiments, the second aqueous solution comprises t-butanol, ethanol, and water as solvents.

In some embodiments, the volume ratio of the amount of water to the amount of the polar organic solvent is in a range from about 1:1 to about 200:1. In some embodiments, the volume ratio of the amount of water to the amount of the polar organic solvent is in a range from about 1.5:1 to about 50:1. In some embodiments, the volume ratio of the amount of water to the amount of the polar organic solvent is in a range from about 1.5:1 to about 10:1. In some embodiments, the volume ratio of the amount of water to the amount of the polar organic solvent is in a range from about 1.5:1 to about 5:1. In some embodiments, the volume ratio of the amount of water to the amount of the polar organic solvent is in a range from about 1.75:1 to about 3:1. In some embodiments, the volume ratio of the amount of water to the amount of the polar organic solvent is in a range from about 2:1 to about 2.5:1. In some embodiments, the volume ratio of the amount of water to the amount of the polar organic solvent is about 1.5:1, about 2:1, about 2.2:1, about 2.3:1, about 2.4:1, about 2.5:1, about 2.6:1, about 3:1, about 4:1, about 5:1, about 6:1, about 7:1, about 8:1, or about 9:1.

In some embodiments, the organic solution is added to the first aqueous solution to form a second aqueous solution. In some embodiments, the organic solution is added dropwise to the first aqueous solution to form a second aqueous solution. In some embodiments, the first aqueous solution is added to the organic solution to form a second aqueous solution. In some embodiments, the mixing is performed with agitation. In some embodiments, the mixing is performed with stirring. In some embodiments, the mixing is performed with shaking.

In some embodiments, the addition is done at the temperature from about 0° C. to about 35° C. In some embodiments, the addition is done at the temperature from about 0° C. to about 25° C. In some embodiments, the addition is done at the temperature from about 0° C. to about 10° C. In some embodiments, the addition is done at the temperature from about 0° C. to about 5° C. In some embodiments, the addition is done at the temperature from about 5° C. to about 10° C.

In some embodiments, the range of pH in the second aqueous solution is from about 3 to about 11, from about 4 to about 10, from about 5 to about 9, from about 7 to about 10, from about 7.5 to about 9.5, from about 6 to about 9, or from about 5.5 to about 9.5.

Removal of Solvents from the Second Aqueous Solution

In some embodiments, the solvents including both water and organic solvent are removed from the second aqueous solution to provide a solid composition. In some embodiments, the solvents including both water and organic solvent are removed from the second aqueous solution simultaneously to provide a solid composition. In some embodiments, the solvents are removed by lyophilization.

In some embodiments, the second aqueous solution is filtered before removal of solvents. For example, the second aqueous solution can be filtered by a 0.22 micron filter before removal of solvents.

As used herein, the term "micron" refers to a unit of measure of one one-thousandth of a millimeter.

Reconstitution of the Solid Composition

In some embodiments, the solid composition is mixed with water. In some embodiments, the solid composition is mixed with an aqueous solution of 0.45% saline and 2.5% Dextrose. In some embodiments, the aqueous solution is a 0.9% saline solution. In some embodiments, the aqueous solution is a 5% Dextrose solution. In some embodiments, the mixing is the addition of water or the water solution to the solid. In some embodiments, the mixing is the addition of the solid to water or the water solution. In some embodiments, the mixing reconstitutes the solid. In some embodiments, the mixing yields a clear aqueous solution. In some embodiments, the range of pH in the reconstituted solution is from about 5 to about 11, from about 6 to about 10, from about 7 to about 9, from about 5.5 to about 9.5, from about 6.5 to about 9.5, or from about 8 to about 9.

Composition Prepared by the Process

In some embodiments, the present disclosure provides a composition comprising Cabazitaxel, human serum albumin, and arginine as described herein, produced by a method comprising the steps of:

(i) obtaining an organic solution of Cabazitaxel in a polar water-miscible organic solvent;

(ii) obtaining a first aqueous solution comprising human serum albumin and arginine; and (iii) mixing the organic solution of Cabazitaxel and the first aqueous solution to obtain a second aqueous solution comprising the composition comprising Cabazitaxel, human serum albumin, and arginine.

In some embodiments, the human serum albumin and the Cabazitaxel in the composition have a ratio by weight of no less than about 120:1. In some embodiments, the human serum albumin and the Cabazitaxel in the composition have a ratio by weight of no less than about 150:1. In some embodiments, the human serum albumin and the Cabazitaxel in the composition have a ratio by weight of no less than about 200:1. In some embodiments, the human serum albumin and the Cabazitaxel in the composition have a ratio by weight of no less than about 300:1. In some embodiments, the Cabazitaxel and the human serum albumin in the composition are in a ratio by weight from about 1:250 to about 1:600. In some embodiments, the Cabazitaxel and the human serum albumin in the composition are in a ratio by weight from about 1:300 to about 1:500. In some embodiments, the Cabazitaxel and the human serum albumin in the composition are in a ratio by weight from about 1:300 to about 1:400. In some embodiments, the Cabazitaxel and the human serum albumin in the composition are in a ratio by weight from about 1:320 to about 1:450. In some embodiments, the Cabazitaxel and the human serum albumin in the composition are in a ratio by weight from about 1:320 to about 1:400. In some embodiments, the Cabazitaxel and the human serum albumin in the composition are in a ratio by weight from about 1:320 to about 1:380. In some embodiments, the Cabazitaxel and the human serum albumin in the composition are in a ratio by weight from about 1:300 to about 1:800. In some embodiments, the Cabazitaxel and the human serum albumin in the composition are in a ratio by weight from about 1:330 to about 1:450. In some embodiments, the Cabazitaxel and the human serum albumin in the composition are in a ratio by weight from about 1:320 to about 1:400. In some embodiments, the Cabazitaxel and the human serum albumin in the composition are in a ratio by weight from about 1:330 to about 1:400. In some embodiments, the Cabazitaxel and the human serum albumin in the composition are in a ratio by weight from about 1:330 to about 1:400. In some embodiments, the Cabazitaxel and the human serum albumin in the composition are in a ratio by weight from about 1:330 to about 1:350. In some embodiments, the Cabazitaxel and the human serum albumin in the composition are in a ratio by weight from about 1:330 to about 1:500. In some embodiments, the Cabazitaxel and the human serum albumin in the composition are in a ratio by weight from about 1:330 to about 1:450. In some embodiments, the Cabazitaxel and the human serum albumin in the composition are in a ratio by weight from about 1:330 to about 1:400. In some embodiments, the Cabazitaxel and the human serum albumin in the composition are in a ratio by weight from about 1:330 to about 1:350. In some embodiments, the Cabazitaxel and the human serum albumin in the composition are in a ratio by weight from about 1:340 to about 1:500. In some embodiments, the Cabazitaxel and the human serum albumin in the composition are in a ratio by weight from about 1:340 to about 1:450. In some embodiments, the Cabazitaxel and the human serum albumin in the composition are in a ratio by weight from about 1:340 to about 1:400. In some embodiments, the Cabazitaxel and the human serum albumin in the composition are in a ratio by weight from about 1:340 to about 1:360. In some embodiments, the Cabazitaxel and the human serum albumin in the composition are in a ratio by weight from about 1:340 to about 1:350. In some embodiments, the Cabazitaxel and the human serum albumin in the composition are in a ratio by weight from about 1:335 to about 1:360. In some embodiments, the Cabazitaxel and the human serum albumin in the composition are in a ratio by weight of about 1:300, about 1:310, about 1:320, about 1:330, about 1:340, about 1:350, about 1:360, about 1:370, about 1:380, about 1:390, or about 1:400. In some embodiments, the Cabazitaxel and the human serum albumin in the composition are in a ratio by weight of about 1:500, about 1:600, about 1:650, about 1:700, about 1:740, about 1:750, or about 1:800. In some embodiments, the Cabazitaxel and the human serum albumin in the composition are in a ratio by weight of about 1:320. In some embodiments, the Cabazitaxel and the human serum albumin in the composition are in a ratio by weight of about 1:330. In some embodiments, the Cabazitaxel and the human serum albumin in the composition are in a ratio by weight of about 1:340. In some embodiments, the Cabazitaxel and the human serum albumin in the composition are in a ratio by weight of about 1:350. In some embodiments, the Cabazitaxel and the human serum albumin in the composition are in a ratio by weight of about 1:360.

In some embodiments, arginine and Cabazitaxel in the composition have a ratio by weight of no less than about 2:1. In some embodiments, arginine and Cabazitaxel in the composition have a ratio by weight of no less than about 3:1. In some embodiments, arginine and Cabazitaxel in the composition have a ratio by weight of no less than about 5:1. In some embodiments, arginine and Cabazitaxel in the composition have a ratio by weight of no less than about 10:1. In some embodiments, arginine and Cabazitaxel in the composition have a ratio by weight of no less than about 15:1.

In some embodiments, the human serum albumin is a native human serum albumin. In some embodiments, the human serum albumin is a native human serum albumin obtained from pools of human plasma. In some embodiments, the human serum albumin is a recombinant human serum albumin. In some embodiments, the human serum albumin is a fatty acid free human serum albumin. In some embodiments, the human serum albumin is essentially fatty acid free.

In some embodiments, the polar water-miscible organic solvent is an alcohol selected from the group consisting of ethanol, isopropanol, t-butanol, and mixtures thereof.

In some embodiments, the polar water-miscible organic solvent is selected from t-butanol, ethanol, and mixtures thereof.

In some embodiments, the polar water-miscible organic solvent is a mixture of t-butanol and ethanol.

In some embodiments, the polar water-miscible organic solvent is a mixture of t-butanol and ethanol, in which the ratio of t-butanol and ethanol by volume is from about 4:1 to about 15:1.

In some embodiments, the polar water-miscible organic solvent is a mixture of t-butanol and ethanol, in which the ratio of t-butanol and ethanol by volume is about 9:1.

In some embodiments, the polar water-miscible organic solvent is acetone.

In some embodiments, the aqueous solvent is water.

In some embodiments, the mixing comprises adding the organic solution to the first aqueous solution. In some embodiments, the adding is carried out dropwise.

In some embodiments, the mixing is carried out at a temperature from about 0° C. to about 25° C. In some embodiments, the mixing is carried out at a temperature from about 0° C. to about 15° C. In some embodiments, the mixing is carried out at a temperature from about 0° C. to about 5° C. In some embodiments, the mixing is carried out at a temperature from about 5° C. to about 10° C. In some embodiments, the mixing is carried out at a temperature from about 5° C. to about 15° C. In some embodiments, the mixing is carried out at a temperature from about 0° C. to about 10° C.

In some embodiments, the volume ratio of the amount of water to the amount of the polar organic solvent is in a range from about 1:1 to about 200:1. In some embodiments, the volume ratio of the amount of water to the amount of the polar organic solvent is in a range from about 1.5:1 to about 50:1. In some embodiments, the volume ratio of the amount of water to the amount of the polar organic solvent is in a range from about 1.5:1 to about 10:1. In some embodiments, the volume ratio of the amount of water to the amount of the polar organic solvent is in a range from about 1.5:1 to about 5:1. In some embodiments, the volume ratio of the amount of water to the amount of the polar organic solvent is in a range from about 1.75:1 to about 3:1. In some embodiments, the volume ratio of the amount of water to the amount of the polar organic solvent is in a range from about 2:1 to about 2.5:1. In some embodiments, the volume ratio of the amount of water to the amount of the polar organic solvent is about 1.5:1, about 2:1, about 2.2:1, about 2.3:1, about 2.4:1, about 2.5:1, about 2.6:1, about 3:1, about 4:1, about 5:1, about 6:1, about 7:1, about 8:1, or about 9:1.

In some embodiments, the methods further comprise the step of removing the organic solvent (e.g. t-butanol, ethanol, and mixtures thereof) and the aqueous solvent (e.g., water) from the second aqueous solution to obtain the solid composition comprising Cabazitaxel, human serum albumin, and arginine as described herein.

In some embodiments, the removing is carried out by lyophilization.

In some embodiments, the composition is a solid formulation.

In some embodiments, the composition is an aqueous formulation. In some embodiments, the aqueous formulation is substantially free of solvent other than water. In some embodiments, the aqueous formulation is free of a surfactant, which is selected from the group consisting of CREMOPHOR® surfactants and Polysorbate 80. In some embodiments, the aqueous formulation is a clear aqueous solution. In some embodiments, the aqueous formulation is a clear aqueous solution for at least 1 hour, at least 2 hours, at least 3 hours, at least 4 hours, at least 8 hours, at least 24 hours, at least 48 hours, or at least 72 hours.

In some embodiments, the concentration of Cabazitaxel in the aqueous formulation is from about 0.02 mg per 1 ml to about 0.5 mg per 1 ml of the aqueous solvent. In some embodiments, the concentration of Cabazitaxel in the aqueous formulation is from about 0.05 mg per 1 ml to about 0.2 mg per 1 ml of the aqueous solvent. In some embodiments, the concentration of Cabazitaxel in the aqueous formulation is about 0.1 mg per 1 ml of the aqueous solvent. In some embodiments, the concentration of Cabazitaxel in the aqueous formulation is about 0.08 mg per 1 ml of the aqueous solvent. In some embodiments, the concentration of Cabazitaxel in the aqueous formulation is about 0.12 mg per 1 ml of the aqueous solvent.

In some embodiments, the aqueous formulation is a clear aqueous solution, wherein the aqueous formulation is substantially free of solvent other than water, and wherein the concentration of Cabazitaxel in the aqueous formulation is from about 0.02 mg per 1 ml to about 0.5 mg per 1 ml of the aqueous solvent. In some embodiments, the aqueous formulation is a clear aqueous solution, wherein the aqueous formulation is substantially free of solvent other than water, and wherein the concentration of Cabazitaxel in the aqueous formulation is from about 0.05 mg per 1 ml to about 0.2 mg per 1 ml of the aqueous solvent. In some embodiments, the aqueous formulation is a clear aqueous solution, wherein the aqueous formulation is substantially free of solvent other than water, and wherein the concentration of Cabazitaxel in the aqueous formulation is about 0.1 mg per 1 ml, about 0.08 mg per 1 ml, about 0.09 mg per 1 ml, about 0.11 mg per 1 ml, or about 0.12 mg per 1 ml of the aqueous solvent.

In some embodiments, the present disclosure provides a pharmaceutical composition comprising the composition as prepared by a process as described herein, and a pharmaceutically acceptable carrier.

In some embodiments, the present disclosure provides a method of treating a cancer, the method comprising the step of administering to a subject in need thereof a therapeutically effective amount of the pharmaceutical composition comprising the composition as prepared by a process as described herein.

In some embodiments, the cancer is a solid tumor cancer. In some embodiments, the cancer is a prostate cancer.

EXAMPLES

Example 1: Composition Comprising Cabazitaxel, Human Serum Albumin (HSA), and Arginine (A) 4.32 ml of water; or (B) 36 mg of L-arginine (Arg) dissolved in 4.32 ml of water were added to 2 different round bottom flasks, each with 4.08 ml of 20% Human Albumin solution for infusion (816 mg HSA), respectively. After the flasks were put in an ice bath, Cabazitaxel (2.4 mg) dissolved in a mixed solvent (3.24 ml t-butanol and 0.36 ml ethanol) was added into each of the 2 flasks dropwise with stirring. Upon completion of the addition, the clear solutions were obtained. The resulting clear aqueous solutions were kept at about 5° C. for about 5 hours, and filtered by a 0.22 micron aqueous phase filter. Each filtered solution was divided evenly into 3 glass vials and lyophilized overnight to give white solids.

One vial with the lyophilized product from each experiment was added with 8 ml of 0.9% saline. After the addition of 8 ml of 0.9% saline, a clear aqueous solution was obtained for the vial with L-arginine, and a cloudy solution with precipitation was obtained for the vial without L-arginine.

Example 2: Composition Comprising Cabazitaxel, Human Serum Albumin (HSA), and Arginine (A) 2.4 ml of water were added to a round bottom flask with 3.2 ml of 20% Human Albumin solution for infusion (640 mg HSA); and (B) 12.8 mg of L-arginine (Arg) dissolved in 2.88 ml of water were added to a round bottom flask with 2.72 ml of 20% Human Albumin solution for infusion (544 mg HSA). After the flasks were put in an ice bath, Cabazitaxel (1.6 mg) dissolved in a mixed solvent (2.16 ml t-butanol and 0.24 ml ethanol) was added into each of the 2 flasks dropwise with stirring, respectively. Upon completion of the addition, the clear solutions were obtained. The resulting clear aqueous solutions were kept at about 5° C. for about 5 hours, and filtered by a 0.22 micron aqueous phase filter. Each filtered solution was divided evenly into 2 glass vials and lyophilized overnight to give white solids.

One vial with the lyophilized product from each experiment was added with 8 ml of 0.9% saline. After the addition of 8 ml of 0.9% saline, a clear aqueous solution was obtained for the vial with L-arginine (the ratio of cabazitaxel and HSA by weight is about 1:340, and ratio of cabazitaxel and L-arginine is about 1:15), and a cloudy solution with precipitation was obtained for the vial without L-arginine (the ratio of cabazitaxel and HSA by weight is about 1:400). This data indicates that adding arginine can significantly increase the water solubility of the formulation.

The clear aqueous solution for the vial with L-arginine stayed clear without precipitation for 4 hours and 24 hours.

Example 3: Composition Comprising Cabazitaxel, Human Serum Albumin (HSA), and Arginine (A) 16 mg of L-arginine (Arg) dissolved in 3.6 ml of water; or (B) 30 mg of L-arginine (Arg) dissolved in 3.6 ml of water were added to 2 different round bottom flasks, each with 3.4 ml of 20% Human Albumin solution for infusion (680 mg HSA), respectively. After the flasks were put in an ice bath, Cabazitaxel (2 mg) dissolved in a mixed solvent (2.7 ml t-butanol and 0.3 ml ethanol) was added into each of the 2 flasks dropwise with stirring. Upon completion of the addition, the clear solutions were obtained. The resulting clear aqueous solutions were kept at about 5° C. for about 3 hours, and filtered by a 0.22 micron aqueous phase filter. Each filtered solution was divided evenly into 2 glass vials and lyophilized overnight to give white solids.

One vial with the lyophilized product from each experiment was added with 10 ml of 0.9% saline. After the addition of 10 ml of 0.9% saline, a clear aqueous solution was obtained for the both vials. The clear aqueous solution for the both vials stayed clear without precipitation for 7 hours, 24 hours, and 48 hours.

Example 4: Composition Comprising Cabazitaxel, Human Serum Albumin (HSA), and Arginine (A) 1 mg of L-arginine (Arg) dissolved in 1.8 ml of water; (B) 5 mg of L-arginine (Arg) dissolved in 1.8 ml of water; or (C) 10 mg of L-arginine (Arg) dissolved in 1.8 ml of water were added to 3 different round bottom flasks, each with 1.7 ml of 20% Human Albumin solution for infusion (340 mg HSA), respectively. After the flasks were put in an ice bath, Cabazitaxel (1 mg) dissolved in a mixed solvent (1.35 ml t-butanol and 0.15 ml ethanol) was added into each of the 3 flasks dropwise with stirring. Upon completion of the addition, the clear solutions were obtained. The resulting clear aqueous solutions were kept at about 5° C. for about 5 hours, and filtered by a 0.22 micron aqueous phase filter. Each filtered solution was divided evenly into 2 glass vials and lyophilized overnight to give white solids.

One vial with the lyophilized product from each experiment was added with 5 ml of 0.9% saline. After the addition of 5 ml of 0.9% saline, a clear aqueous solution was obtained for the vial from the experiment adding 10 mg of L-arginine, and a cloudy solution with precipitation was obtained for the vials from the experiments adding 1 mg of L-arginine or 5 mg of L-arginine.

The clear aqueous solution for the vial from the experiment adding 10 mg of L-arginine stayed clear without precipitation for 7 hours.

Example 5: Measure pH Value of the Clear Aqueous Solution of Composition Comprising Cabazitaxel, Human Serum Albumin (HSA), and Arginine 75 mg of L-arginine (Arg) dissolved in 9 ml of water was added to a round bottom flask with 8.5 ml of 20% Human Albumin solution for infusion (1.7 g HSA). After the flask was put in an ice bath, Cabazitaxel (5 mg) dissolved in a mixed solvent (6.75 ml t-butanol and 0.75 ml ethanol) was added into the flask dropwise with stirring. Upon completion of the addition, the clear solution was obtained. The resulting clear aqueous solution was kept at about 5° C. for about 3 hours, and filtered by a 0.22 micron aqueous phase filter. The filtered solution was divided evenly into 5 glass vials and lyophilized overnight to give white solids.

10 ml of 0.9% saline was added into one glass vial with the lyophilized product to give a clear aqueous solution. The clear aqueous solution was kept at about 25° C. and measured for pH value. The pH value of the clear aqueous solution is 8.81 (3 measurements: 8.81, 8.82, and 8.81).

10 ml of 5% dextrose solution was added into one glass vial with the lyophilized product to give a clear aqueous solution. The clear aqueous solution was kept at about 25° C. and measured for pH value. The pH value of the clear aqueous solution is 8.78 (3 measurements: 8.77, 8.79, and 8.79).

Example 6: Measure the Correlation Between HPLC Peak Area and the Cabazitaxel Concentration Methanol solutions of cabazitaxel in 8 different concentrations, 0.025 mg/mL, 0.0375 mg/mL, 0.05 mg/mL. 0.075 mg/mL, 0.1 mg/mL, 0.15 mg/mL, 0.2 mg/mL and 0.25 mg/mL, were prepared. The 8 cabazitaxel methanol solutions were analyzed in HPLC. The peak area and concentration of cabazitaxel were correlated using linear regression. The linear regression data is shown as below.
Y (peak area)=8680+2.854E7*X (concentration), R=0.99998, P<0.0001.

Example 7: Measure the Cabazitaxel Concentrations in the Clear Aqueous Solutions before or after the filtration at 0 hour, 1 hours, 3 hours, 5 hours, and 24 hours 48 mg of L-arginine (Arg) dissolved in 5.76 ml of water was added to a round bottom flask with 5.44 ml of 20% Human Albumin solution for infusion (1088 mg HSA). After the flask was put in an ice bath, Cabazitaxel (3.2 mg) dissolved in a mixed solvent (4.32 ml t-butanol and 0.48 ml ethanol) was added into the flask dropwise with stirring. Upon completion of the addition, the clear solution was obtained. The resulting clear aqueous solution was kept at about 5° C. for about 3 hours, and filtered by a 0.22 micron aqueous phase filter. The filtered solution was divided evenly into 4 glass vials and lyophilized overnight to give white solids.

Three of glass vials with the lyophilized product were added with 8 ml of 0.9% saline in each vial. Immediately after the lyophilized solids in the vials were dissolved, the aqueous solution of the three vials were combined, and 1 ml of the aqueous solution was taken out from the 24 ml solution. Then 1 ml of the solution was named as the solution CB-0-0h. To 300 µl of the solution CB-0-0h was added 700 µl of acetonitrile. The mixture was vortexed for seconds and then centrifuged at 4,000 g for 5 minutes. The supernatants were removed and collected followed by injection on HPLC. The same procedure was repeated one more time for the solution DC-0-0h. Based on the HPLC data and the measurement data of Example 6, the Cabazitaxel concentrations of the supernatants prepared from solution of CB-0-0h have been calculated and shown in the Table 1.

TABLE 1

| Solution Number | Cabazitaxel Concentration (mg/ml) | Average Cabazitaxel Concentration (mg/ml) |
|---|---|---|
| CB-0-0h-1 | 0.02326 | 0.02352 |
| CB-0-0h-2 | 0.02377 | |

At 1 hour, additional 5 ml of the aqueous solution was taken out from the remaining aqueous solution in the vial. Then 1 ml of the solution was taken out from the 5 ml aqueous solution and filtered by a 0.22 micron aqueous phase filter to give the solution CB-1-1h, and the remaining 4 ml of the solution was filtered by the same 0.22 micron aqueous phase filter at 1 ml at a time to give the solutions CB-2-1h, CB-3-1h, CB-4-1h, and CB-5-1h. To 300 µl of the solution CB-5-1h was added 700 µl of acetonitrile. The mixture was vortexed for seconds and then centrifuged at 4,000 g for 5 minutes. The supernatant was removed and collected followed by injection on HPLC. The same procedure was repeated one more time for the solution CB-5-1h. Based on the HPLC data and the measurement data of Example 6, the Cabazitaxel concentrations of the supernatants prepared from solution of CB-5-1h have been calculated and shown in the Table 2. At 1 hour, the Cabazitaxel concentration of the aqueous solution after the filtration was about 99.7% of the Cabazitaxel concentration of the aqueous solution at 0 hour before the filtration.

TABLE 2

| Solution Number | Cabazitaxel Concentration (mg/ml) | Average Cabazitaxel Concentration (mg/ml) |
|---|---|---|
| CB-5-1h-1 | 0.02346 | 0.02345 |
| CB-5-1h-2 | 0.02343 | |

At 3 hour, 5 ml of the aqueous solution was taken out from the remaining aqueous solution in the vial. The experiments were done for the 5 ml of the aqueous solution taken out at 3 hour using the same protocol as for the 5 ml of the aqueous solution taken out at 1 hour. Based on the HPLC data and the measurement data of Example 6, the Cabazitaxel concentrations of the supernatants prepared from solution of CB-5-3h have been calculated and shown in the Table 3. At 3 hour, the Cabazitaxel concentration of the aqueous solution after the filtration was about 98.7% of the Cabazitaxel concentration of the aqueous solution at 0 hour before the filtration.

TABLE 3

| Solution Number | Cabazitaxel Concentration (mg/ml) | Average Cabazitaxel Concentration (mg/ml) |
|---|---|---|
| CB-5-3h-1 | 0.02308 | 0.02321 |
| CB-5-3h-2 | 0.02334 | |

At 5 hour, 5 ml of the aqueous solution was taken out from the remaining aqueous solution in the vial. The experiments were done for the 5 ml of the aqueous solution taken out at 5 hour using the same protocol as for the 5 ml of the aqueous solution taken out at 1 hour. Based on the HPLC data and the measurement data of Example 6, the Cabazitaxel concentrations of the supernatants prepared from solution of DC-5-5h have been calculated and shown in the Table 4. At 5 hour, the Cabazitaxel concentration of the aqueous solution after the filtration was about 97.1% of the Cabazitaxel concentration of the aqueous solution at 0 hour before the filtration.

TABLE 4

| Solution Number | Cabazitaxel Concentration (mg/ml) | Average Cabazitaxel Concentration (mg/ml) |
|---|---|---|
| CB-5-5h-1 | 0.02277 | 0.02283 |
| CB-5-5h-2 | 0.02288 | |

At 24 hour, 5 ml of the aqueous solution was taken out from the remaining aqueous solution in the vial. The experiments were done for the 5 ml of the aqueous solution taken out at 24 hour using the same protocol as for the 5 ml of the aqueous solution taken out at 1 hour. Based on the HPLC data and the measurement data of Example 6, the Cabazitaxel concentrations of the supernatants prepared from solution of DC-5-24h have been calculated and shown in the Table 5. At 24 hour, the Cabazitaxel concentration of the aqueous solution after the filtration was about 83.3% of the Cabazitaxel concentration of the aqueous solution at 0 hour before the filtration.

TABLE 5

| Solution Number | Cabazitaxel Concentration (mg/ml) | Average Cabazitaxel Concentration (mg/ml) |
|---|---|---|
| CB-5-24h-1 | 0.01960 | 0.01959 |
| CB-5-24h-2 | 0.01958 | |

OTHER EMBODIMENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A composition comprising Cabazitaxel, or a pharmaceutically acceptable salt thereof, human serum albumin, and arginine, or a pharmaceutically acceptable salt thereof, wherein the human serum albumin and the Cabazitaxel, or a pharmaceutically acceptable salt thereof, in the composition have a ratio by weight of no less than about 120:1, and wherein arginine, or a pharmaceutically acceptable salt thereof, and Cabazitaxel, or a pharmaceutically acceptable salt thereof, in the composition have a ratio by weight of no less than about 1:1.

2. The composition of claim 1, wherein arginine, or a pharmaceutically acceptable salt thereof, and Cabazitaxel, or a pharmaceutically acceptable salt thereof, in the composition have a ratio by weight of no less than about 5:1.

3. The composition of claim 1, wherein arginine, or a pharmaceutically acceptable salt thereof, and Cabazitaxel, or a pharmaceutically acceptable salt thereof, in the composition have a ratio by weight from about 5:1 to about 150:1.

4. The composition of claim 1, wherein Cabazitaxel, or a pharmaceutically acceptable salt thereof, and human serum albumin in the composition are in a ratio by weight from about 1:300 to about 1:500.

5. The composition of claim 1, wherein Cabazitaxel, or a pharmaceutically acceptable salt thereof, and human serum albumin in the composition are in a ratio by weight from about 1:300 to about 1:400.

6. The composition of claim 1, wherein the human serum albumin in the composition is a native human serum albumin.

7. The composition of claim 1, wherein the composition is a solid formulation.

8. The composition of claim 1, wherein the composition is an aqueous formulation.

9. The composition of claim 8, wherein the aqueous formulation has pH value from about 5 to about 9.

10. The composition of claim 8, wherein the aqueous formulation is a clear aqueous solution.

11. The composition of claim 8, wherein the aqueous formulation is a clear aqueous solution for at least 2 hours.

12. A pharmaceutical composition comprising the composition of claim 1, and a pharmaceutically acceptable carrier.

13. A method of treating a cancer selected from bladder cancer, brain cancer, breast cancer, colorectal cancer, cervical cancer, gastrointestinal cancer, genitourinary cancer, head and neck cancer, lung cancer, ovarian cancer, pancreatic cancer, prostate cancer, renal cancer, skin cancer, and testicular cancer, the method comprising a step of administering to a subject in need thereof a therapeutically effective amount of a pharmaceutical composition of claim 12.

14. The method of claim 13, wherein the cancer is prostate cancer.

15. A liquid composition comprising Cabazitaxel and human serum albumin, wherein the human serum albumin and the Cabazitaxel in the composition have a ratio by weight of no less than about 120:1, wherein arginine, or a pharmaceutically acceptable salt thereof, and the Cabazitaxel, or a pharmaceutically acceptable salt thereof, in the composition have a ratio by weight of no less than about 1:1, and wherein the composition comprises water, t-butanol, and ethanol.

16. The composition of claim 15, wherein the liquid composition is a clear aqueous solution.

17. The composition of claim 15, wherein Cabazitaxel, or a pharmaceutically acceptable salt thereof, and human serum albumin in the composition are in a ratio by weight from about 1:300 to about 1:500.

18. The composition of claim 15, wherein the liquid composition has pH value from about 5 to about 9.

19. A method of treating a cancer selected from sarcoma, angiosarcoma, fibrosarcoma, rhabdomyosarcoma, liposarcoma, myxoma, rhabdomyoma, fibroma, lipoma, teratoma, non-small cell lung cancer, bronchogenic carcinoma squamous cell, undifferentiated small cell, undifferentiated large cell, adenocarcinoma, alveolar bronchiolar carcinoma, bronchial adenoma, lymphoma, chondromatous hamartoma, mesothelioma, gastrointestinal cancer, cancer of the esophagus, squamous cell carcinoma, leiomyosarcoma, cancer of the stomach, carcinoma, cancer of the pancreas, ductal adenocarcinoma, insulinoma, glucagonoma, gastrinoma, carcinoid tumor, vipoma, cancer of the small bowel, carcinoid tumors, Kaposi's sarcoma, leiomyoma, hemangioma, neurofibroma, cancer of the large bowel or colon, tubular adenoma, villous adenoma, hamartoma, genitourinary tract cancer, cancer of the kidney adenocarcinoma, Wilm's tumor, nephroblastoma, leukemia, cancer of the bladder, cancer of the urethra, transitional cell carcinoma, cancer of the prostate, cancer of the testis, seminoma, embryonal carcinoma, teratocarcinoma, choriocarcinoma, interstitial cell carcinoma, fibroadenoma, adenomatoid tumors, liver cancer, hepatoma hepatocellular carcinoma, cholangiocarcinoma, hepatoblastoma, hepatocellular adenoma, bone cancer, osteogenic sarcoma, osteosarcoma, malignant fibrous histiocytoma, chondrosarcoma, Ewing's sarcoma, malignant lymphoma, reticulum cell sarcoma, multiple myeloma, malignant giant cell tumor, chordoma, osteochrondroma, osteocartilaginous exostoses, benign chondroma, chondroblastoma, chondromyxofibroma, osteoid osteoma giant cell tumor, nervous system cancer, cancer of the skull, osteoma, granuloma, xanthoma, osteitis deformans, cancer of the meninges meningioma, meningiosarcoma, gliomatosis, cancer of the brain, astrocytoma, medulloblastoma, glioma, ependymoma, germinoma, pinealoma, glioblastoma multiforme, oligodendroglioma, schwannoma, retinoblastoma, congenital tumors, cancer of the spinal cord, meningioma, gynecological cancer, cancer of the uterus, endometrial carcinoma, cancer of the cervix, cervical carcinoma, pre tumor cervical dysplasia, cancer of the ovaries, ovarian carcinoma, serous cystadenocarcinoma, mucinous cystadenocarcinoma, unclassified carcinoma, granulosa-theca cell tumor, Sertoli Leydig cell tumor, dysgerminoma, malignant teratoma, cancer of the vulva, intraepithelial carcinoma, melanoma, cancer of the vagina, clear cell carcinoma, botryoid sarcoma, embryonal rhabdomyosarcoma, cancer of the fallopian tubes, hematologic cancer, cancer of the blood, acute myeloid leukemia, chronic myeloid leukemia, acute lymphoblastic leukemia, chronic lymphoblastic leukemia, chronic lymphocytic leukemia, myeloproliferative diseases, myelodysplastic syndrome, Hodgkin's lymphoma, non-Hodgkin's lymphoma, Waldenstrom's macroglobulinemia, skin cancer, malignant melanoma, basal cell carcinoma, Kaposi's sarcoma, moles dysplastic nevi, angioma, dermatofibroma, keloids, psoriasis, adrenal gland cancer, and neuroblastoma, the method comprising a step of administering to a subject in need thereof a therapeutically effective amount of a pharmaceutical composition of claim 12.

\* \* \* \* \*

UNITED STATES PATENT AND TRADEMARK OFFICE
CERTIFICATE OF CORRECTION

PATENT NO. : 11,413,265 B2
APPLICATION NO. : 16/982252
DATED : August 16, 2022
INVENTOR(S) : Qun Sun It is certified that error appears in the above-identified patent and that said Letters Patent is hereby corrected as shown below:

On the Title Page

Item (56), Column 2, Line 1, delete "al.," "Phase" and insert -- al., "Phase --

Item (56), Column 2, Line 14, delete "semm" and insert -- serum --

In the Claims

Column 33, Line 27, Claim 19, delete "osteochrondroma," and insert -- osteochondroma, --

Signed and Sealed this
Twenty-second Day of November, 2022

*Katherine Kelly Vidal*

Katherine Kelly Vidal
*Director of the United States Patent and Trademark Office*